(12) United States Patent
Lee et al.

(10) Patent No.: US 9,814,907 B2
(45) Date of Patent: Nov. 14, 2017

(54) RECOMBINANT SELF-ASSEMBLING PROTEIN COMPRISING TARGET-ORIENTED PEPTIDE AND USE THEREOF

(71) Applicant: Korea University Research and Business Foundation, Seoul (KR)

(72) Inventors: Jeewon Lee, Seoul (KR); Koo-Chul Kwon, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 28 days.

(21) Appl. No.: 14/849,379

(22) Filed: Sep. 9, 2015

(65) Prior Publication Data

US 2016/0074511 A1    Mar. 17, 2016

Related U.S. Application Data

(63) Continuation of application No. PCT/KR2014/004193, filed on May 9, 2014.

(30) Foreign Application Priority Data

May 10, 2013   (KR) .................. 10-2013-0053291
May 9, 2014    (KR) .................. 10-2014-0055902

(51) Int. Cl.
| | |
|---|---|
| *A61K 47/69* | (2017.01) |
| *A61N 5/06* | (2006.01) |
| *C07K 14/005* | (2006.01) |
| *A61K 49/04* | (2006.01) |
| *C07K 14/71* | (2006.01) |

(52) U.S. Cl.
CPC .......... *A61N 5/062* (2013.01); *A61K 49/0428* (2013.01); *C07K 14/005* (2013.01); *C07K 14/71* (2013.01); *C07K 2319/20* (2013.01); *C07K 2319/21* (2013.01); *C07K 2319/32* (2013.01); *C12N 2730/10122* (2013.01); *C12N 2730/10123* (2013.01); *C12N 2730/10133* (2013.01); *C12N 2810/855* (2013.01)

(58) Field of Classification Search
CPC .......... A61K 2300/00; A61K 2039/505; A61K 47/48276; A61K 38/00; A61K 51/088; A61K 31/7088; A61K 38/08; A61K 38/10; A61K 47/48338; A61K 47/48384; A61K 47/48761; A61K 47/48776; A61K 48/005; A61K 39/12; A61K 9/5184; C12N 2770/28123; C12N 2770/28134; C12N 2770/32323; C12Q 2600/136; C12Q 1/18; C12Q 1/68

See application file for complete search history.

(56) References Cited

FOREIGN PATENT DOCUMENTS

| | | |
|---|---|---|
| KR | 10-2008-0035926 A | 4/2008 |
| KR | 10-2011-0027998 A | 3/2011 |
| KR | 10-2011-0090347 A | 8/2011 |
| KR | 10-2012-0052501 A | 5/2012 |
| KR | 10-2013-0039672 A | 4/2013 |

OTHER PUBLICATIONS

Zheng et al. Chemistry Physics Letters, 2011, vol. 506, No. 1-3, pp. 76-80.*
Kim, Dongwook et al., "Heptameric Targeting Ligands against EGFR and HER2 with High Stability and Avidity", PLOS ONE, vol. 7, Issue 8, 13 pages (Aug. 2012).

* cited by examiner

*Primary Examiner* — Bao Li
(74) *Attorney, Agent, or Firm* — Mintz Levin Cohn Ferris Glovsky and Popeo, P.C.; Kongsik Kim; Katherine C. Jensen

(57) ABSTRACT

The present invention relates to a recombinant self-assembled protein comprising a target-oriented peptide and a use thereof. The recombinant self-assembled protein according to the present invention, comprising a target-oriented peptide, does not require an additional process for providing target-orientedness, and is thus capable of delivering a desired drug to a target tissue or target cell without using additives, such as chemical binders or stabilizers; therefore, the protein can be used for photothermal therapy, drug delivery, imaging, or the like. In particular, according to the present invention, it is possible to prepare gold-protein nanoparticle fusions in which uniform high-density gold nanoparticles having target-orientedness are bound to protein surfaces, without an additional process of surface stabilization or process for providing target-orientedness. Compared with conventional gold nanoparticles, the gold-protein nanoparticle fusions according to the present invention show structural stability against pH variation and concentration variation, and also have excellent target-orientedness; therefore, the fusions can bring a dramatic enhancement to the utilization of gold nanoparticles in photothermal therapy.

17 Claims, 26 Drawing Sheets

RECOMBINANT SELF-ASSEMBLING PROTEIN COMPRISING TARGET-ORIENTED PEPTIDE AND USE THEREOF

CROSS-REFERENCE TO RELATED APPLICATION

This is a continuation of International Application No. PCT/KR2014/004193 filed on May 9, 2014, which claims priority to Korean Application No. 10-2013-0053291 filed on May 10, 2013 and Korean Application No. 10-2014-0055902 filed on May 9, 2014. The applications are incorporated herein by reference.

INCORPORATION-BY-REFERENCE OF SEQUENCE LISTING

The contents of the sequence listing text file named "58301-095C01US_SEQUENCE_LISTING_ST25.txt", which was created on Jul. 25, 2017 and is 9,101 bytes in size, is hereby incorporated by reference in its entirety.

TECHNICAL FIELD

The present invention relates to a recombinant self-assembled protein comprising a target-oriented peptide, and the use thereof.

BACKGROUND ART

Despite tremendous advances in medicine, patients who are under drug therapy or radiotherapy usually suffer from cytotoxicity or side effects attributed to the systemic administration of drugs, or the side effects of radiotherapy such as the mutation or death of normal cells. The accurate delivery of drugs such as contrast agents or therapeutic agents to target tissues could allow for the diagnosis or therapy of diseases without causing side effects in normal cells or tissues. Accordingly, extensive research has been directed toward drug targeting in order to diagnose or treat diseases without side effects.

Drug targeting or targeted drug delivery is typically accomplished by chemically or physically linking a drug with an antibody, a peptide, a ligand, or a polymer specific for or targeting tissues or cells to which the drug is to be delivered. However, physiochemical properties of drugs do not always permit easy linkage with antibodies, peptides, ligands, etc. Further, if used for chemical or physical bonding, a binder or a stabilizer may cause negative effects on pharmaceutical properties or biotoxicity of drugs. Hence, there is still a technical need for drug targeting methods free of such problems.

Of targeted drug delivery methods for killing cancer cells, photothermal therapy using gold nanoparticles may be applied for the effective treatment of cancer. Gold nanoparticles, ranging in size up to tens of nanometers, exhibit intrinsic optical properties through the quantumization of surface electrons, and find applications in a variety of fields including single electron devices, chemical sensors, biosensors, drug delivery, and catalysts. For instance, Professor Halas and Professor West's research team at Rice University synthesized a gold nanoshell and applied it to thermal therapy for the necrosis of cancer cells. The gold nanoparticle is a nanostructure composed of a silica core coated with a gold nanoshell. Depending on the ratio of thickness between the core and the outer shell, the light absorption wavelength can be adjusted from a visible light range to a near infrared (NIR) range. The research team synthesized a gold nanoshell having a large NIR absorption cross section. The gold nanoshell was conjugated at the surface with an antibody specific for cancer cells, and then was applied to cancer cells and irradiated with an NIR continuous wave laser. The NIR light absorbed by the gold nanoshell was converted into heat by which cancer cells can be effectively necrotized. Less apt to be absorbed into biological tissues, light in an NIR region of 800 nm to 1200 nm can reach deeper in the biological tissues than can visible light. Hence, irradiation of NIR light can bring about a desirable thermal treatment effect, with the production of a minimal incision area.

However, conventional synthesis methods of gold nanoparticles, such as chemical reductive reactions, typically need the use of metal compounds, solvents, reducing agents, or stabilizers. One of main barriers to the use of gold nanoparticles in the medical field is the toxicity caused by such chemical additives.

In addition, the production of stable gold nanoparticles requires a surface modification. When they are subjected to a pH change or are highly concentrated, gold nanoparticles, if not surface modified, undergo condensation due to structural instability, and are altered in size and morphology. Therefore, an additional surface stabilization technology must be needed for gold nanoparticles. For use in drug targeting, gold nanoparticles allow antibodies or targeting peptides to be exposed on the surface thereof via a chemical linkage. In this regard, uniform exposure of antibodies or peptides at a high density is a limitative point.

Generally, sodium citrate is used as a condensation nucleus for metal ions in synthesizing gold nanoparticles. At a pH of 7.0 or higher, tyrosine can offer a standard reduction potential at which gold ions can be reduced. Thus, a peptide containing such amino acids can be used to reduce gold ions and produce gold nanoparticles stabilized on the surface of the peptide (KR2012-0052501). However, the method disclosed in KR2012-0052501 is merely a technique in which gold-affinitive proteins or gold ion reducing peptides are reacted with gold precursors to aggregate gold nanoparticles around the proteins or peptides. Thus, this method is not only difficult to apply to the morphological or dimensional control of gold nanoparticles, but also requires additional chemical linkages for providing target directionality.

SUMMARY

The present invention provides a recombinant self-assembled protein comprising a target-oriented peptide, which does not necessitate an additional target-orienting process, and the use thereof. In addition, the present invention provides a gold-protein nanoparticle fusion capable of exposing uniform, high-density target-oriented peptides, without an additional process of surface stabilization or of target orienting, and the use thereof.

In accordance with an aspect thereof, the present invention addresses a recombinant self-assembled protein comprising a target-oriented peptide fused into a self-assembled protein; a recombinant self-assembled protein comprising a target-oriented peptide and a gold ion reducing peptide; a gold-protein particle fusion in which a gold nanoparticle is formed on a recombinant self-assembled protein nanoparticle composed of copies of the recombinant self-assembled protein; and use of the gold-protein particle fusion in photothermal therapy or as a contrast agent.

The recombinant self-assembled protein nanoparticle according to the present invention is a spherical protein particle with a nanosize diameter, which is constructed as a monomer of the recombinant self-assembled protein comprising the target-oriented peptide fused into the self-assembled protein are self-assembled.

As used herein, the term "self-assembled protein" refers to a protein, a sub-protein unit, or a peptide that can spontaneously form a structural organization or pattern with another protein, producing an aggregate. Advantageously, the self-assembled protein can be used to form a protein nanoparticle according to the present invention because it is possible without a separate operation. Designed to be structurally stable by self-assembly, the protein nanoparticles of the present invention can be used to reproducibly achieve very high uniformity in particle size. Furthermore, the protein nanoparticles of the present invention are biocompatible and biodegradable, without causing the toxicity attributed to the nanoparticles remaining after use in the body.

Meanwhile, the term "target-oriented peptide," as used herein, refers to a peptide or an antibody that is capable of binding to the surface of cells, such as cancer cells or inflammatory cells, thus driving the recombinant self-assembled nanoparticles according to the present invention to a target site to be treated or diagnosed, such as the cancer cells or inflammatory cells. The target-oriented peptide may be introduced onto a surface of the recombinant self-assembled protein nanoparticles.

In the present invention, a monomer of the recombinant self-assembled protein nanoparticle in which the target-oriented peptide is fused into the self-assembled protein may be expressed using an expression vector.

Accordingly, so long as it can be easily inserted into an expression vector and does not influence the structure of the self-assembled protein according to the present invention, any peptide may be used irrespective of sequence and length. In this regard, the target-oriented peptides may be substituted with a wide variety of peptidyl antagonists, peptide hormones, or hormone analogs (e.g., somatostatins, bombesin, cholecystokinin, gastrin analog) that are known to bind to receptors specifically overexpressed on tissues or cells affected with particular diseases, instead of actual hormones, so as to interrupt signal transduction.

In one exemplary embodiment of the present invention, the self-assembled protein may be a human-derived self-assembled protein. In the present invention, the term "human-derived self-assembled protein or a protein nanoparticle comprising the same" is intended to encompass a humanized self-assembled protein or a humanized protein nanoparticle.

In another exemplary embodiment of the present invention, the self-assembled protein may be ferritin, but is not limited thereto. Ferritin is a protein consisting of 24 identical subunits, each having a heavy chain and a light chain, and forms a spherical hollow shell in vivo by self-assembly.

According to another exemplary embodiment of the present invention, the self-assembled protein may be a ferritin-heavy chain (hereinafter referred to as "FTN-H").

Without being limited to the theory, the target-oriented peptide may be fused into the N- or C-terminus of ferritin. Located on a surface of the protein nanoparticle, the target-oriented peptide fused into ferritin provides strong target directionality, and thus can effectively deliver the recombinant self-assembled protein nanoparticles of the present invention into a target site.

In accordance with another exemplary embodiment of the present invention, the self-assembled protein of the present invention may be a hepatitis B virus (HBV) capsid protein.

Approximately 180-240 copies of the hepatitis B virus (HBV) capsid protein useful for the preparation of the recombinant self-assembled protein of the present invention can form a spherical protein nanoparticle through self-assembly. Using genetic recombination technology, the HBV capsid protein can be produced on a mass scale. Particularly when a foreign protein is fused into a spike region of the HBV capsid protein, the resulting fused protein is expressed in such a manner that the foreign protein is exposed on the surface of the fused protein. Accordingly, the present invention can allow for specific targeting by expressing a target-oriented peptide at a spike region of HBV.

Also, the present invention provides a recombinant self-assembled protein nanoparticle comprising the recombinant self-assembled proteins. By the target-oriented peptides exposed on the surface thereof, the recombinant self-assembled protein nanoparticle according to the present invention can effectively be driven toward a target site of interest where a desired aim, such as photothermal treatment, drug delivery or imaging, is accomplished.

Capable of providing target directionality, the recombinant self-assembled protein nanoparticle according to the present invention finds applications in various fields. For instance, the use of the recombinant self-assembled protein nanoparticle can be extended by further comprising a fusion peptide or protein in addition to the target-oriented peptide.

In one exemplary embodiment of the present invention, the recombinant self-assembled protein nanoparticle according to the present invention may be used for photothermal therapy, drug delivery, or imaging.

Also, contemplated in accordance with another exemplary embodiment of the present invention is a recombinant self-assembled protein comprising a target-oriented peptide fused into a self-assembled protein, and a gold ion reducing peptide.

The recombinant self-assembled protein nanoparticle for photothermal therapy comprises a gold ion reducing peptide. When gold precursors react with the recombinant self-assembled protein nanoparticles, gold nanoparticles are formed on the recombinant self-assembled protein nanoparticles as gold ions are reduced. Herein, an aggregate in which a gold nanoparticle is formed on the recombinant self-assembled protein nanoparticle is called a gold-protein particle fusion.

In one exemplary embodiment of the present invention, the self-assembled protein may be an HBV capsid protein. In this regard, the target-oriented peptide may be introduced into a spike, or an N- or C-terminus of the recombinant HBV capsid protein. According to another exemplary embodiment of the present invention, the target-oriented peptide may be introduced into a spike of the recombinant HBV capsid protein.

In the present invention, a monomer of an HBV capsid protein nanoparticle in which a target-oriented peptide and a gold ion reducing peptide are fused into an HBV capsid protein is expressed through an expression vector.

Accordingly, so long as it can be easily inserted into an expression vector and does not influence the function and the gold ion reducing peptide and the structure of the self-assembled protein according to the present invention, any peptide may be used irrespective of sequence and length. In this regard, the target-oriented peptides may be substituted with a variety of peptidyl antagonists, peptide hormones, or hormone analogs (e.g., somatostatins, bombesin, cholecystokinin, gastrin analog) that are known to bind to receptors specifically overexpressed on tissues or cells affected with particular diseases, instead of actual hormones, so as to interrupt signal transduction.

Without being limited to the theory, the target-oriented peptide useful in one exemplary embodiment of the present invention may target EGFR (epidermal growth factor receptor), which is specific for human breast cancer cells, or EDB (human fibronectin extradomain B), which can be used as a biomarker for head and neck cancer.

In one exemplary embodiment, the target-oriented peptide may be introduced into a spike site of the recombinant HBV capsid protein. Another exemplary embodiment of the present invention offers a method for providing the gold-protein particle fusion of the present invention with target directionality) by expressing a peptide (EGFR affibody) specific for a human breast cancer cell line (MDA MB-468 tumor model) in a form fused to the spike of the HBV capsid protein, using a genetic recombination technique. For example, when positioned between two peptide segments (a.a. 1-78 and a.a. 81-149) of the HBV capsid protein, a target-oriented peptide can be exposed at a spike site of the HBV capsid protein at a high density. In another exemplary embodiment of the present invention, a plurality of target-oriented peptides may be inserted into the recombinant HBV capsid protein. Insertion of more target-oriented peptides brings about a higher exposure density of target-oriented peptides, thus further promoting the migration of the gold-protein particle fusion of the present invention to the target tissue.

Over chemical techniques, a genetic engineering technique, when used for the fusion of a target-oriented peptide to the self assembling protein, has an advantage of controlling surface exposure frequency and position of the target-oriented peptide. In order to achieve a low surface exposure frequency of the target-oriented peptide, for example, the recombinant self-assembled protein comprising the target-oriented peptide and the gold ion reducing peptide, and the recombinant self-assembled protein comprising the gold ion reducing peptide only are combined at a proper ratio to give a recombinant self-assembled protein nanoparticle.

The gold ion reducing peptide contained in the recombinant self-assembled protein is an essential component for forming the gold-protein particle fusion according to the present invention. The term "gold ion reducing peptide", as used herein, refers to a peptide providing a standard reduction potential at which the gold ions contained in the gold precursors can be reduced. Typically, the gold ion reducing peptide may have an amino acid sequence comprising two or more tyrosine residues (Yn, n≥2), histidine residues (Hn, n≥2), or cysteine residues (Cn, n≥2), or an amino acid sequence containing at least one of tyrosine, histidine, and cysteine. By way of example, the gold ion reducing peptide may have an amino acid sequence of YYY, YYYYYY (SEQ ID NO: 20), or YAHHYAHHYAADY (SEQ ID NO: 21). In one exemplary embodiment of the present invention, the gold ion reducing peptide may be hexatyrosine. The gold ion reducing peptide may be introduced into a spike region or an N- or C-terminus of the recombinant self-assembled protein. In one exemplary embodiment of the present invention, the gold ion reducing peptide is introduced into an N- or C-terminus of the recombinant self-assembled protein. According to another exemplary embodiment of the present invention, a hexatyrosine peptide is expressed as a gold ion reducing peptide in a form fused into the N terminus of the self assembling protein, so that the gold ion reducing peptide can be exposed at a high degree of integration on the surface of the recombinant self-assembled protein nanoparticle.

In accordance with another exemplary embodiment of the present invention, the recombinant self-assembled protein may further comprise a gold nanoparticle size-controlling peptide. The gold nanoparticle size-controlling peptide serves as a physical barrier to prevent the gold nanoparticle from infinitely increasing in size when the gold nanoparticle is formed by reacting the gold ion reducing peptide with a gold precursor. So long as it forms a physical barrier to the size of the gold nanoparticle, any peptide may be used in the art, without particular limitations imposed on the kind of the peptide. In one exemplary embodiment of the present invention, a biotinylated peptide is used as the gold nanoparticle size-controlling peptide in a form fused to the recombinant HBV capsid protein. During the expression of the fused protein, biotin is added to prevent the gold nanoparticle from excessively growing. In contrast, the group in which a biotinylated peptide is not fused cannot control the size of the gold nanoparticles, with aggregation occurring upon concentration or pH adjustment.

In another exemplary embodiment of the present invention, the recombinant self-assembled protein may a linker peptide between the gold ion reducing peptide and the gold nanoparticle size-controlling peptide. The linker peptide is unreactive and contains multiple glycines. Occupying a proper space between the gold ion reducing peptide and the gold nanoparticle size-controlling peptide, the linker peptide allows for the sufficient growth of gold particles and simultaneously prevents the gold ions from being excessively reduced, and provides structural stability.

The linker peptide may be long enough to secure a proper space between the gold ion reducing peptide and the gold nanoparticle size-controlling peptide. Thus, the linker peptide may vary in length, depending on kinds and sizes of the gold ion reducing peptide and the gold nanoparticle size-controlling peptide. For instance, the linker peptide may be 5 to 20 amino acids long, e.g., a 5 to 15 amino acids long.

For ease of isolation, the recombinant self-assembled protein may further comprise a peptide such as a histidine tag, a FLAG (DYKDDDDK (SEQ ID NO: 22), or a GST tag.

The recombinant self-assembled protein according to the present invention can be prepared by a method comprising a) cloning a gene coding for an HBV self-assembled protein, b) cloning a gene including a nucleotide sequence coding for a target-oriented peptide for insertion into the self-assembled protein, c) constructing an expression vector containing the clones by ligation, and d) transforming the expression vector into a host to express the recombinant self-assembled protein.

The gene clone for the self-assembled protein may contain nucleotide sequences coding for the gold ion reducing peptide, the linker, and the peptide for isolation and purification.

Meanwhile, the recombinant self-assembled protein is one of 180-240 molecules that are self assembled to form a recombinant self-assembled protein nanoparticle. Accordingly, contemplated in accordance with another aspect of the present invention is a recombinant self-assembled protein nanoparticle made from many copies of the recombinant self-assembled protein.

As used herein, the term "gold-protein particle fusion" means a fusion in which a gold nanoparticle is formed on the self-assembled protein nanoparticle composed of many copies of the recombinant self-assembled protein. When a gold precursor is reacted with the recombinant self-assembled protein nanoparticle, the gold ion is reduced to form a gold nanoparticle on the recombinant self-assembled protein nanoparticle. Hence, the present invention provides a method for preparing a gold-protein particle fusion, comprising reacting a gold precursor with the recombinant self-assembled protein nanoparticle to form a gold nanoparticle on the recombinant self-assembled protein nanoparticle, and the gold-protein particle fusion thus prepared.

In the present invention, a gold precursor that can be used in reaction with the recombinant self-assembled protein nanoparticle may be exemplified by chloro(trimethylphosphine)gold ($AuClP(CH_3)_3$), potassium tetrachloroaurate (III) ($KAuCl_4$), sodium chloroaurate ($NaAuCl_4$), chloroauric acid ($HAuCl_4$), sodium bromoaurate ($NaAuBr_4$), gold chloride ($AuCl$), gold (III) chloride ($AuCl_3$), and gold bromide ($AuBr_3$).

The reaction of the recombinant self-assembled protein nanoparticle with a gold precursor may be carried out at a pH of 7.0 to 10.

Without being limited to the theory, the reaction between the recombinant self-assembled protein nanoparticle and the gold precursor may be conducted for 2 to 16 hrs. When the reaction time is less than 2 hrs, insufficient reduction may result. On the other hand, a negative influence may be imposed on the proteins when a reaction time exceeds 16 hrs. The reaction time may vary, depending on various factors including kinds, concentrations of the participants of the reaction, such as the recombinant self-assembled protein nanoparticle, the gold precursors, etc.

The reaction between the recombinant self-assembled protein nanoparticle and the gold precursor starts in the presence of a reducing agent. Unless a strong reducing powder is provided, it is difficult to form gold particles from gold ions because the protein generally has structural stability. Although a reducing agent is used, the method of the present invention has advantages over a chemical method of preparing gold nanoparticles in that the reaction can be carried out at room temperature rather than high temperatures and the gold-protein nanoparticle fusion has high structural stability without requiring an additional surface treatment. In one exemplary embodiment of the present invention, examples of the reducing agent include $NaBH_4$ and $H_2O_2$, but are not limited thereto.

The gold-protein particle fusion has a structure in which a gold nanoparticle having a controlled size is formed on a surface of the recombinant self-assembled protein nanoparticle.

The gold nanoparticle of the gold-protein particle fusion may have a diameter of 1 nm or less. The size of the gold nanoparticle may vary depending on the kind of the recombinant self-assembled protein, and can be adjusted by controlling the gap between the gold particle reducing peptide and the gold nanoparticle size-controlling peptide, that is, the length of the linker peptide, the concentration of the reducing agent, reaction time, etc. For example, since the recombinant HBV capsid protein nanoparticle has a size of about 35 to 36 nm, the gold-protein particle fusion according to the present invention in which the gold particle is formed on the protein nanoparticle exhibits physical properties similar to those of the gold nanoparticle 35-40 nm in size.

The gold-protein particle fusion of the present invention exhibits a very uniform particle size distribution because the gold particles are formed on the recombinant self-assembled protein nanoparticles. In addition, since sizes of the gold particles on the protein nanoparticles are controlled using the gold nanoparticle size-controlling peptide, the target-oriented peptide is not hindered by the sizes. In addition, the gold-protein particle fusion is free from the problem of safety and toxicity because it is made of biocompatible materials that can be degradable in vivo and is free of additives for chemically modifying surfaces of gold nanoparticles.

The gold-protein particle fusion according to the present invention can be very useful for photothermal therapy. In one exemplary embodiment of the present invention, when a laser is irradiated while the concentration of the gold-protein particle fusion is increased, the fusion increases in temperature to up to 55° C., which exceeds the necrotic temperature of cancer or inflammatory cells (generally 43 to 45° C.). In addition, the gold-protein particle fusion comprising a target-oriented peptide specific for breast cancer cells, when injected to the body, was monitored to effectively target human breast cancer cells.

Therefore, the present invention provides the use of the gold-protein particle fusion in preparing a medication for photothermal therapy, a pharmaceutical composition for photothermal therapy comprising the gold-protein particle fusion and a pharmaceutically acceptable carrier, and a method of performing photothermal therapy comprising administering the gold-protein particle fusion to a subject, and irradiating the subject with light.

Modalities of photothermal therapy for killing cancer cells or inflammatory cells are well known in the art.

Because cancer cells are vulnerable particularly to heat, they can be selectively killed by positioning a photosensitive material at a local site where the cancer cells are located, and externally stimulating the photosensitive material to generate heat. Hence, the photothermal therapy has less negative influence on normal cells, compared to chemical therapy or radiation therapy.

Photothermal therapy can be used to eliminate inflammatory cells or lesion tissues of rheumatoid arthritis as well as cancer. Arthritis of joints involves inflammation of the synovial membrane surrounding joints (synovitis). Once synovitis is induced, more inflammatory cells infiltrate into the synovial membrane and synovial cells proliferate. In this regard, the angiogenesis promotes the growth and activation of the synovial tissue. With the progression of rheumatoid arthritis, the inflammation leads to the destruction of the joint cartilage and bone around the synovial tissue. Releasing various cytokines, particularly TNF-α, interleukin (IL)-1, and IL-6, T and B lymphocytes are involved in the inflammation of joints. Photothermal therapy, if used to eliminate the lesion found in rheumatoid arthritis, can improve a therapeutic effect on rheumatoid arthritis. The photothermal therapy may be carried out in combination with the administration of nonsteroidal anti-inflammatory drugs (NSAIDs) or disease-modifying anti-rheumatic drugs (DMARDs).

The light used for the heat generation of the gold-protein particle fusion according to the present invention may have a wavelength of 600 nm to 1,500 nm, for example, 800 nm to 1,200 nm, but is not limited to the wavelength. In order for the gold-protein particle fusion to generate heat, light is irradiated for a time of 1 sec to 10 hrs, for example, 1 sec to 1 hour, 1 sec to 30 min, 1 sec to 10 min, or 1 sec to 1 min. The irradiation time may vary depending on various factors including the amount of cells to be killed, the coverage of lesion, and the severity of disease, etc.

Because it contains gold nanoparticles on the surface of the protein, the gold-protein particle fusion according to the present invention, after administered, allows for bioimaging through X-ray or CT scanning, thus visibly monitoring migration to and arrival at a target site. Accordingly, another aspect of the present invention addresses the use of the gold-protein particle fusion in preparing a contrast agent, a contrast agent composition comprising the gold-protein particle fusion and a pharmaceutically acceptable carrier, and a bioimaging method comprising administering the gold-protein particle fusion to a subject, and irradiating X-ray to the subject.

The pharmaceutically acceptable carrier used in the pharmaceutical composition for photothermal therapy or in the contrast agent composition may be a typical carrier or vehicle of the present invention.

Examples of the pharmaceutically acceptable carrier include ion-exchanged alumina, aluminum stearate, lecithin, a serum protein, a buffer, water, a salt or electrolyte, colloidal silica, magnesium trisilicate, polyvinylpyrrolidone, a cellulosic substrate, polyethylene glycol, sodium carboxymethylcellulose, polyarylate, wax, polyethylene glycol, and wool fat, but are not limited thereto. In addition to the ingredients, the composition of the present invention may further comprise a lubricant, a humectant, an emulsifier, a suspension agent, a preservative, etc.

In one exemplary embodiment, the composition according to the present invention may be formulated into an aqueous solution for parenteral administration. Preferably, a Hank's solution, a Ringer's solution, or a buffer, such as physically buffered saline, may be used. As for an aqueous injection suspension, its viscosity may be increased by containing a substance, such as sodium carboxymethyl cellulose, sorbitol, or dextran.

A preferred composition of the present invention may be an aqueous or oily suspension in the form of a sterile injectable preparation. This suspension may be formulated according to techniques known in the art using a suitable dispersant or humectant, and a suspending agent. The sterile injectable preparation may also be a sterile injectable solution or suspension in a non-toxic parenterally-acceptable diluent or solvent. Among acceptable vehicles and solvents that may be employed are mannitol, water, a Ringer's solution, and an isotonic sodium chloride solution. In addition, sterile, fixed oils are typically employed as a solvent or suspension medium. For this purpose, fixed oils of low irritability, including a synthetic mono- or di-glyceride, may be used.

Not necessitating an additional target directing process, the recombinant self-assembled protein comprising the target-oriented peptide is capable of deliver a drug of interest to a target tissue or cell without employing an a supplementary agent such as a chemical binder or a stabilizer, and thus can be applied to photothermal therapy, drug delivery, or bioimaging. Particularly, according to the present invention, a target-directing gold-protein nanoparticle fusion in which gold nanoparticles with uniform sizes are bound at a high density onto a surface of the protein can be constructed without employing an additional surface stabilizing or target directing process. Compared to conventional gold nanoparticles, the gold-protein nanoparticle fusion of the present invention has higher structural stability against pH and concentration changes, and exhibits higher target directability, thus bringing about an exceptional improvement in photothermal therapy.

DETAILED DESCRIPTION

Figure 1A:
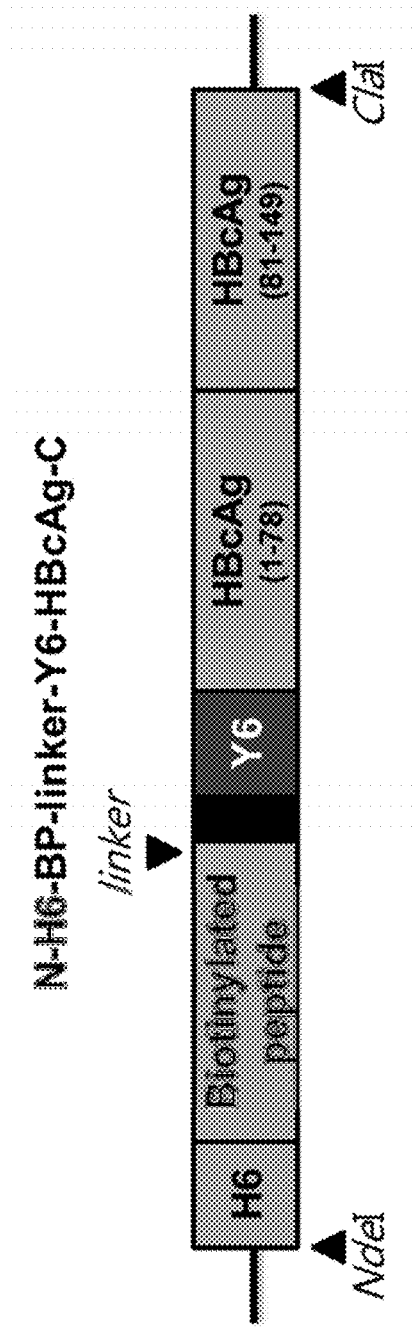
FIGS. 1A and 1B show schematic views of expression vectors for preparing a gold-protein nanoparticle fusion.

Advantages and characteristics of the present invention, and a method of achieving them will become clear with reference to the following Examples as mentioned below in detail. However, the present invention is not limited to the following Examples, and various types of the present invention will be implemented in various manners. The Examples are disclosed merely to provide a complete description of the present invention and to provide complete understanding of the present invention to those skilled in the art to which the present invention belongs, and the present invention is only defined by the appended claims.

EXAMPLES

Example 1: Construction of Expression Vector for Biosynthesis of HBV Capsid-Derived Chimeric Nanoparticle Two gene clones respectively encoding N-NdeI-H6(hexahistidine)-BP(Biotinylated peptides)-Y6(hexatyrosine)-HBVcAg(1-78)-XhoI-C(SEQ ID NO: 2) and N-BamHI-HBVcAg(81-149)-ClaI-C(SEQ ID NO: 3), both derived from an HBV core protein gene (HBVcAg), were acquired by extension PCR using an HBV capsid gene sequence (SEQ ID NO: 1, a 1901-2452 sequence of the NCBI Nucleotide accession number: AF286594) as a template in the presence of primers 1-5, and primer 6 as listed in Table 1, below. In order to substitute P79A80 of HBVcAg with EGFR affibody (Epidermal Growth Factor Receptor 1), 5'-XhoI-EGFR affibody-BamHI-3'(SEQ ID NO: 4) was obtained by PCR. These gene clones were ligated in serial to plasmid pT7-7 to construct a recombinant plasmid expression vector pT7-7-N-H6-BP-Y6-HBVcAg(1-78)-EGFR affibody-HBVcAg (81-149)-C (FIG. 1), which codes the gene N-H6-BP-Y6-HBVcAg(1-78)-EGFR affibody-HBVcAg(81-149)-C(SEQ ID NO: 5). The sequences for all the recombinant constructed plasmid expression vector were identified by complete DNA sequencing after agarose-gel isolation.

Information on primer sequences and templates relevant to the preparation of HBV capsid-derived chimeric nanoparticles will be described in detail, below (Table 1).

1) A first segment was obtained by extension PCR using an HBV capsid protein gene (SEQ ID NO: 1, a 1901-2452 sequence of NCBI Nucleotide accession number: AF286594) as a template in the presence of primers 1 to 5 containing the restriction recognition site NdeI, and primer 6 containing the restriction recognition site XhoI. As a result, a 5'-NdeI-H6-BP-Y6-HBV capsid protein (amino acid sequence 1-78)-XhoI-3' sequence (SEQ ID NO: 2) was obtained as a PCR product.

2) For a second segment, PCR was performed on an HBV capsid protein gene as a template in the presence of primers 7 and 8 containing the restriction recognition sites BamHI and ClaI, respectively. As a result, a 5'-BamHI-HBV capsid protein (amino acid sequence 81-149)-ClaI-3' sequence (SEQ ID NO: 3) was obtained as a PCR product.

3) A third segment was obtained by performing PCR on an EGFR affibody nucleotide sequence as a template in the presence of primers 9 and 10 containing the restriction recognition sites XhoI and BamHII, respectively. As a result, a 5'-XhoI-EGFR affibody-BamHI-3' sequence (SEQ ID NO: 4) was acquired as a PCR product.

The PCR products obtained above were sequentially inserted into a pT7-7 vector to construct a recombinant expression vector pT7-7-N-H6-BP-Y6-HBVcAg(1-78)-EGFR affibody-HBVcAg(81-149)-C, which can express an HBV capsid-derived functional moiety (hexatyrosine) capable of inducing the reduction of gold ions, and an EGFR affibody binding specifically to human breast cancer cells (FIG. 1A).

Figure 1B:
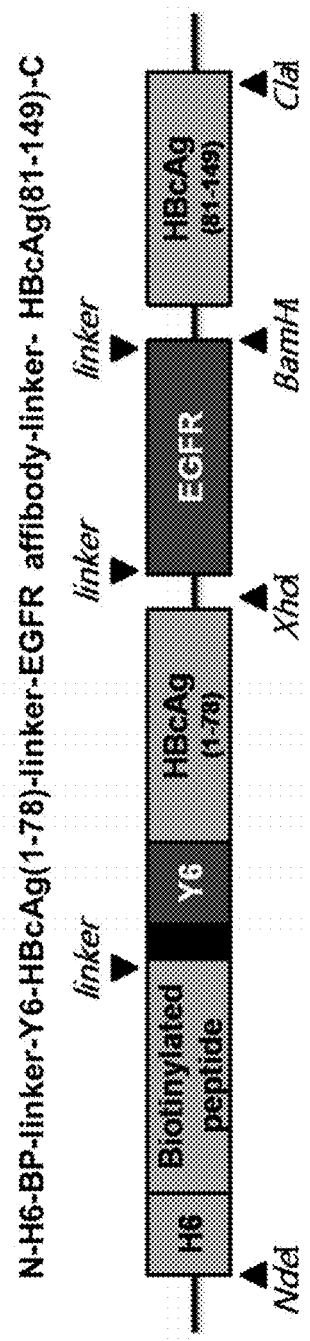

4) Comparison was made of the affinity of EGFR affibodies for cancer cells. For this, extension PCR was performed using primers 1 to 5, and primer 8 containing ClaI. The PCR product thus obtained was inserted into a pT7-7 vector to construct a recombinant expression vector carrying a gene that encodes an HBV capsid-derived functional group (hexatyrosine) capable of inducing the reduction of gold ions. The recombinant expression vector was used as a control for EGFR affibody (FIG. 1B).

TABLE 1

| Primer 1 (SEQ ID NO: 6) | 5' NdeI-H6-BP-Y6-HBcAg1 (1) | CATATGCATCACCATCAC CATCACATGGCGTCTAGT CTGCGT |
|---|---|---|
| Primer 2 (SEQ ID NO: 7) | 5' NdeI-H6-BP-Y6-HBcAg1 (2) | ATGGCGTCTAGTCTGCGT CAGATTCTGGATTCTCAG AAAATGGAATGGCG |
| Primer 3 (SEQ ID NO: 8) | 5' NdeI-H6-BP-Y6-HBcAg1 (3) | CAGAAAATGGAATGGCGT TCTAATGCGGGTGGCTCT GGTGGCGGAAGTGGG |
| Primer 4 (SEQ ID NO: 9) | 5' NdeI-H6-BP-Y6-HBcAg1 (4) | GGTGGCGGAAGTGGGGGAG GCACTGGAGGTGGCGGCGG TGGG TACTATTAC |
| Primer 5 (SEQ ID NO: 10) | 5' NdeI-H6-BP-Y6-HBcAg1 (5) | GGCGGTGGGTACTATTAC TATTACTATGACATTGAC CCGTATAAAGAA |
| Primer 6 (SEQ ID NO: 11) | 3' XhoI-HBcAg78 | CTCGAG GTCTTCCAAAT TACTTCCCA |
| Primer 7 (SEQ ID NO: 12) | 5' BamHI-HBcAg81 | GGATCC TCCAGGGAATTA GTAGTCAGC |
| Primer 8 (SEQ ID NO: 13) | 3' ClaI-HBcAg149 | ATCGAT TTAAACAACAGTA GTTTCCGGAAGTGT |
| Primer 9 (SEQ ID NO: 14) | 5' XhoI-EGFR AFFIBODY | CTCGAG GTGGATAACAAAT TTAACAAA |
| Primer 10 (SEQ ID NO: 15) | 3' BamHI-EGFR AFFIBODY | GGATCCTTTCGGCGCCTGCG CATCGTTCAGTTTTTTCGCT TC |

Example 2: Biosynthesis of HBV Capsid-Derived Chimeric Nanoparticle

The *E. coli* strain BL21(DE3)[F-ompThsdSB(rB-mB-)] was transformed with each of the recombinant expression vectors, followed by selecting ampicillin-resistant transformant. The transformant was cultured in 50 mL of Luria-Bertani (LB) medium (containing 100 mg L-1 ampicillin) in a flask (250 mL Erlenmeyer flask, 37° C., 150 rpm). When absorbance (O.D600) reached about 0.4-0.5, IPTG (Isopropyl-β-D-thiogalactopyranosid) (1.0 mM) was added to induce the expression of the protein. In this regard, the expression was conducted in the presence of biotin (100 μM) to regulate the excessive growth of gold nanopaticles that would be reduced at the N-terminus of the protein. For a control, the recombinant gene was expressed in the absence of biotin (100 μM). After incubation at 20° C. for 16-18 hrs, the medium was centrifuged at 4,500 rpm for 10 min to harvest cell mass. The cell mass was then suspended in 5 ml of a lysis buffer (10 min Tris-HCl buffer, pH 7.5, 10 min EDTA), and lyzed using an ultrasonicator (Branson Ultrasonics Corp., Danbury, Conn., USA). Centrifugation at 13,000 rpm for 10 min separated a supernatant and a precipitate. The supernatant was purified according to the procedure of Example 3, below.

Example 3: Purification of HBV Capsid-Derived Chimeric Nanoparticle

In order to purify a self-assembled EGFR affibody-protein fused protein nanoparticle among the expressed recombinant proteins, the following three-step purification was carried out: 1) Ni2+-NTA affinity chromatography was conducted to separate the recombinant protein on the basis of the binding of the histidine residues fused to the recombinant protein to nickel ions, 2) an ultracentrifugal filter (Amicon Ultra 100K, Millipore, Billerica, Mass.) was used to change the medium of the recombinant protein into a self-assembled buffer (500 mM NaCl 0.50 mM Tris-HCl pH 7.0) for improving the self assembling efficiency of the recombinant protein, with the concomitant concentration of the protein, and 3) sucrose density gradient ultracentrifugation was performed to isolate the self-assembled protein nanoparticle alone. Specification of each step is as follows.

1) Ni2+-NTA Affinity Chromatography

For the purification of the recombinant protein, the transformed *E. coli* was harvested as described above, and the cell pellet was resuspended in 5 mL of a lysis buffer (pH 8.0, 50 mMsodium phosphate, 300 mM NaCl, 20 mM imidazole), and lyzed using a sonicator. After centrifugation of the cell lysate at 13,000 rpm for 10 min, each of the recombinant proteins was separated from the supernatant using an Ni2+-NTA column (Qiagen, Hilden, Germany) (wash buffer: pH 8.0, 50 mM sodium phosphate, 300 mM NaCl, 80 mM imidazole/elution buffer: pH 8.0, 50 mM sodium phosphate, 300 mM NaCl, 200 mM imidazole).

2) Buffer Change for Promoting Self-Assembling, and Concentration

After 3 ml of the recombinant protein eluted by Ni2+-NTA affinity chromatography was loaded to an ultracentrifugal filter (Amicon Ultra 100K, Millipore, Billerica, Mass.), and centrifuged at 5,000 g for 10 min, the column was fully filled with a buffer for self-assembly (500 mM NaCl 0.50 mM Tris-HCl pH 7.0). Again, centrifugation at 5,000 g was conducted until 500 µl of the solution remained in the column. This procedure was three times repeated to adjust a final volume into 1 mL.

3) Sucrose-Gradient Ultracentrifugation

Sucrose was added in various amounts to the buffer for self-assembly to give solutions having sucrose concentrations of 60%, 50%, 40%, 30%, 20%, and 10%. Each of the sucrose solutions (60-20%) was added in an amount of 2 mL in a descending order of the sucrose concentration to an ultracentrifugation tube (ultraclear 13.2 ml tube, Beckman), and then 0.5 ml of the 10% sucrose solution was placed on the layered sucrose solutions. After 1 ml of the recombinant protein in the buffer for self-assembly was loaded onto the 10% sucrose solution, centrifugation at 24,000 rpm for 6 hrs at 4° C. was conducted (Ultracentrifuge L-90k, Beckman). Subsequently, the upper layers (10-40% sucrose) were carefully removed using a pipette and the remainder including 50-60% sucrose solutions was subjected to buffer change into the buffer for self-assembly using the ultracentrifugal filter as described in 2).

Figure 2A:
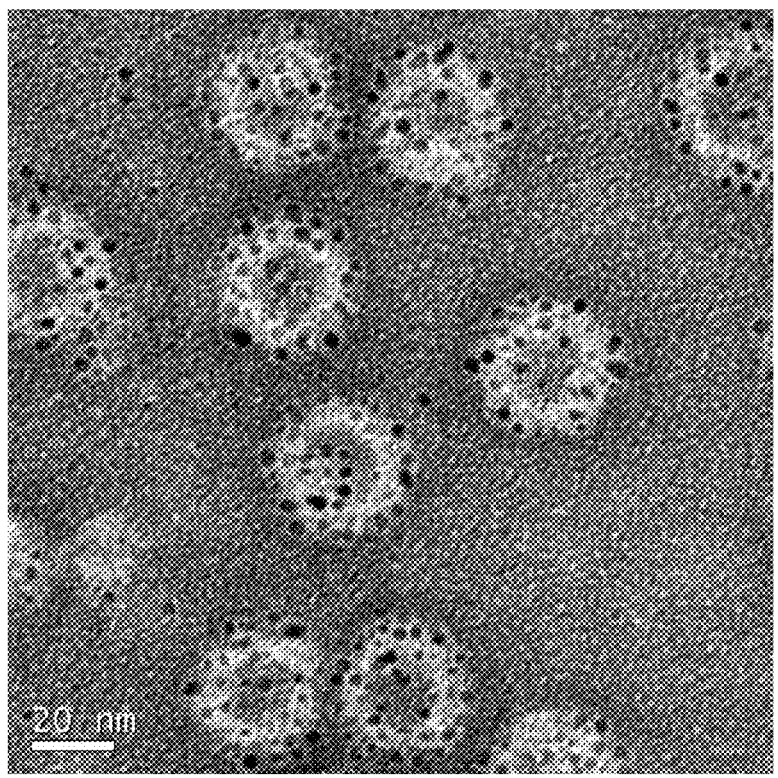
FIGS. 2A through 2C show images of protein nanoparticles, and gold-protein nanoparticle fusions separated and purified after expression in E. coli, as analyzed by TEM (A) and EDX (Energy-dispersive X-ray spectroscopy) (B).
Figure 2B:
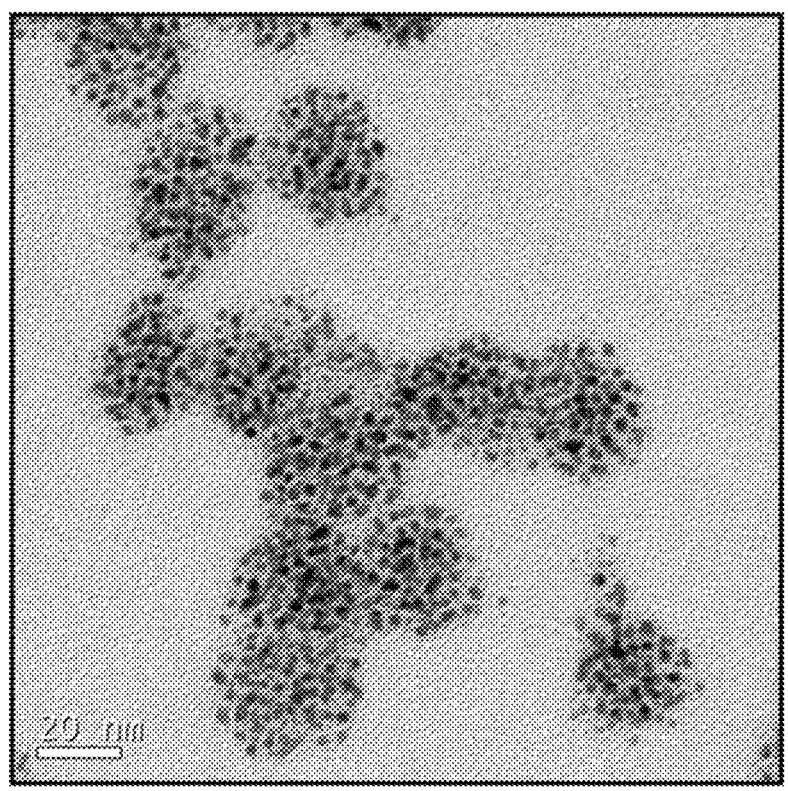
Figure 2C:
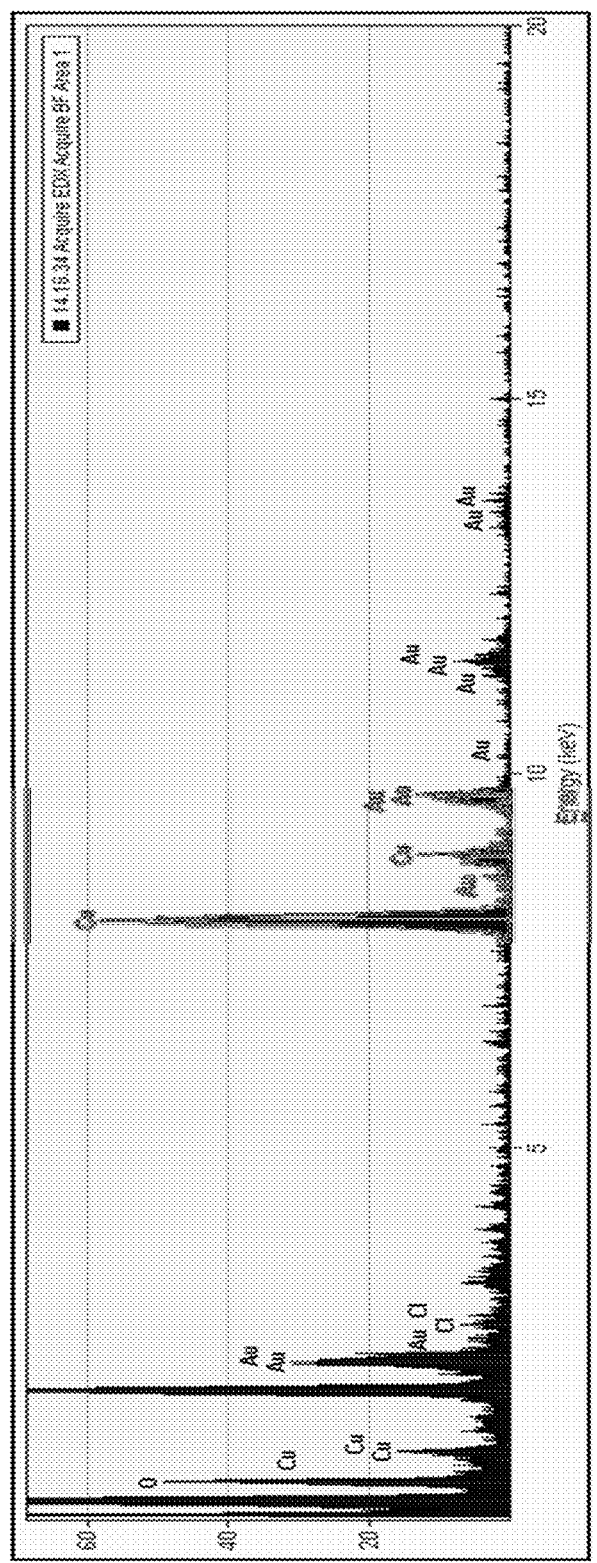

Example 4: Reduction of Gold Ions on HBV Capsid-Derived Chimeric Nanoparticle The HBV capsid-derived chimeric nanoparticle obtained in Example 3 had a hexatyrosine sequence that was linked at the N terminus to a biotynylated peptide. The HBV capsid-derived chimeric nanoparticle in a recombinant protein buffer, pH 7.0 was reacted with $AuClP(CH_3)_3$ chloro (trimethylphosphine) gold (I) for 16 hrs, followed by centrifugation at 13,000 rpm for 10 min at 4° C. The supernatant was withdrawn, and reacted with a 10-fold concentration of the reducing agent NaBH4 for 10 min to afford gold-protein particle fusions in which the size of the gold nanoparticles was regulated by biotin (FIG. 2A) and were not regulated (FIG. 2B).

Example 5: Structural Analysis of HBV Capsid-Derived Chimeric Nanoparticle

Figure 3:
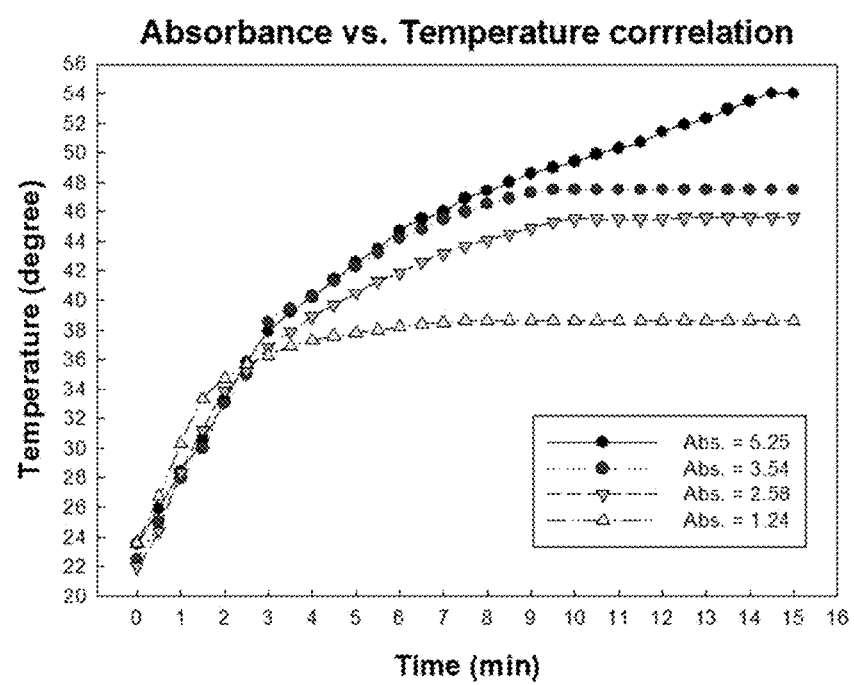
FIG. 3 is a graph in which temperatures are plotted against laser irradiation time (15 min) according to the concentration of the gold-protein nanoparticle fusion.

The recombinant protein nanoparticles purified through the above procedure were structurally analyzed by transmission electron microscopy (TEM). To this end, first, a purified protein sample was placed on carbon-coated copper electron microscope grids, and allowed to dry naturally. The dried sample on the electron microscope grids was incubated at room temperature for 10 min with a 2% (w/v) aqueous uranyl acetate solution, and then washed 3-4 times with distilled water. The protein nanoparticles were found to be spherical nanoparticles with a size of 30-35 nm as observed by a Philips Technai 120 kV electron microscope. The results are shown in FIGS. 3A and 3B. Also, EDX (Energy-dispersive X-ray spectroscopy) showed that the metal bound onto the surface of the fusion was gold.

Example 6: Temperature Increasing Tendency with Concentration of HBV Capsid-Derived Chimeric Gold-Protein Nanoparticle Fusion—In Vitro Examination was made to see whether the gold-protein particle fusion increased in temperature to a point applicable to the photothermal therapy of cancer. In this regard, the gold-protein particle fusion was plated in an amount of 100 µl/well into 96-well plates, and irradiated for 15 min with a laser (655 nm, 200 W) while its absorbance at 530 nm was increased. Temperatures of the gold-protein particle fusion are plotted against time (15 min) according to absorbance in FIG. 3.

Figure 4:
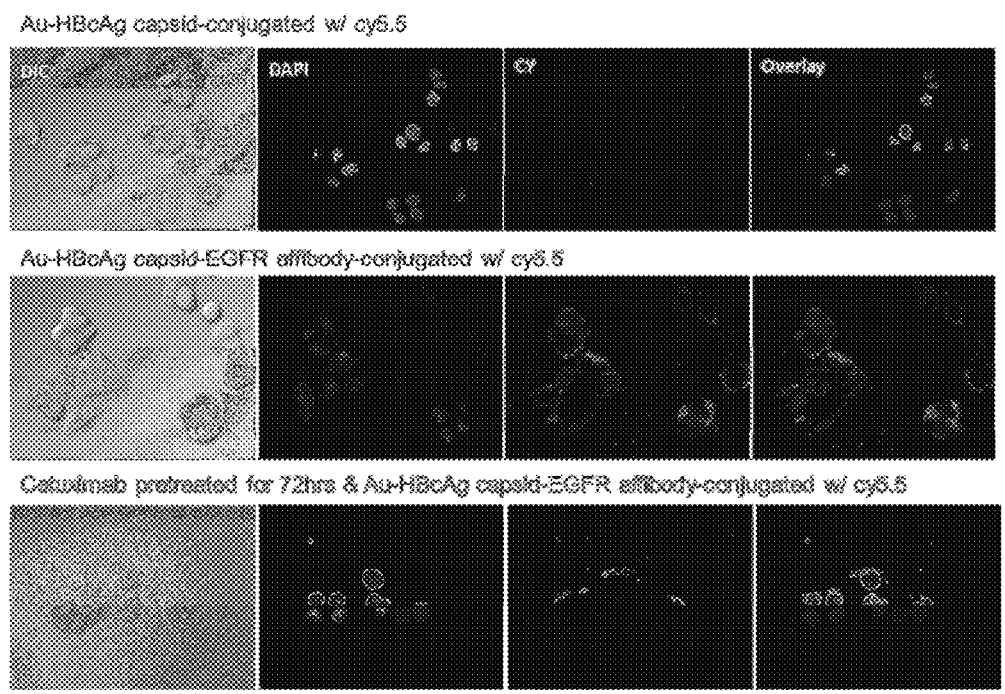
FIG. 4 shows results of targeting experiments in which gold-protein nanoparticle fusions with or without a biodiagnostic peptide (EGFR affibody) specific for breast cancer cells therein are allowed to target a target cancer cell line (MDA MB468).

Example 7: Specific Target Directionality of HBV Capsid-Derived Chimeric Gold-Protein Nanoparticle Fusion Toward Cancer Cell—In Vitro Examination was made to see whether the exposed, targeting peptide EGFR affibody of the gold-protein particle fusion specifically targeted cancer cells. For this, the human breast cancer cell line (MDA MB-468 cell line) was grown on 35-ϕ plates. Separately, the gold-protein particle fusions obtained in Example 1, which contained the EGFR affibody or did not contain the EGFR affibody, was labeled with Cy5.5 ($\lambda$ex=675 nm/$\lambda$em=694 nm) at the N terminus. The human breast cancer cells were incubated for 10 min with the gold-protein particle fusion to monitor the endocytosis of the particle into the cells. Only in the cell group treated with the fusion having the EGFR affibody, Cy5.5 fluorescence was observed. In order to examine whether the EGFR affibody directly targeted an EGF receptor, human breast cancer cells were incubated with cetuximab, which is an anticancer agent functioning as an antibody specific for the EGFR receptor, for 72 hours before the treatment of the breast cancer cells with the gold-protein nanoparticle fusion having the EGFR affibody for 10 min No Cy5.5 fluorescence was observed in the cells, indicating that the EGFR affibody directly targets the EGF receptor of human breast cancer cells (FIG. 4).

Example 8: Necrosis of Cancer Cell by Laser Irradiation

Figure 5A:
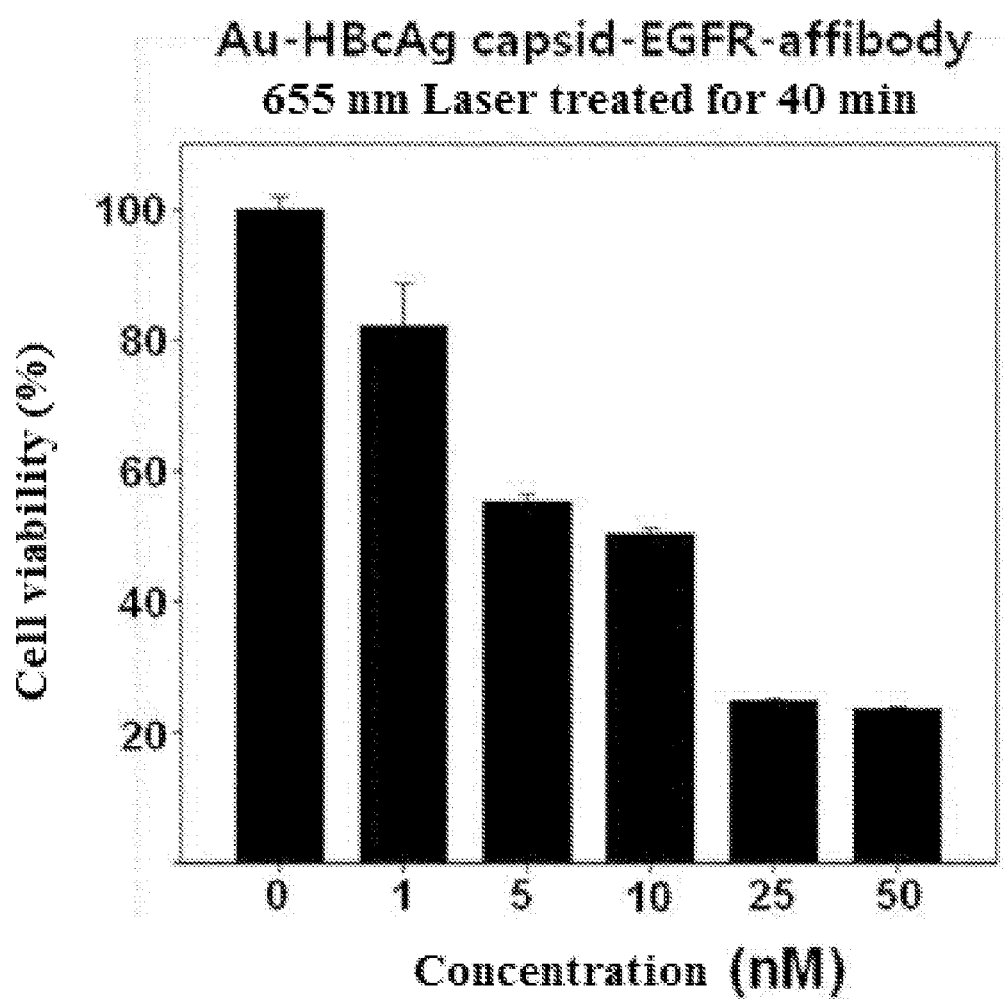
FIG. 5A shows cancer cell viability vs. the concentration of the gold-protein nanoparticle fusion.
Figure 5B:
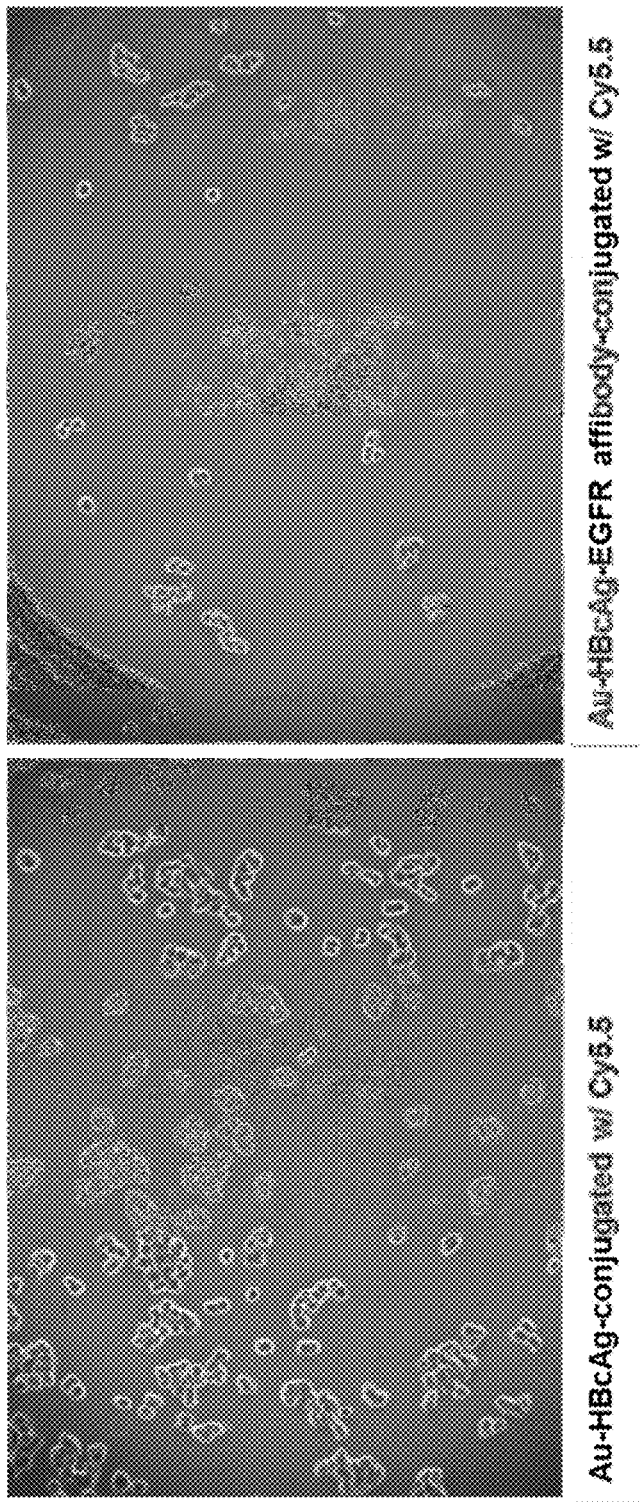
FIG. 5B shows results of photothermal therapy in which gold-protein nanoparticle fusions with or without a biodiagnostic peptide (EGFR affibody) specific for breast cancer cells are allowed to target an object cancer cell line (MDA MB468), followed by irradiating layer for 10 min
Figure 5C:
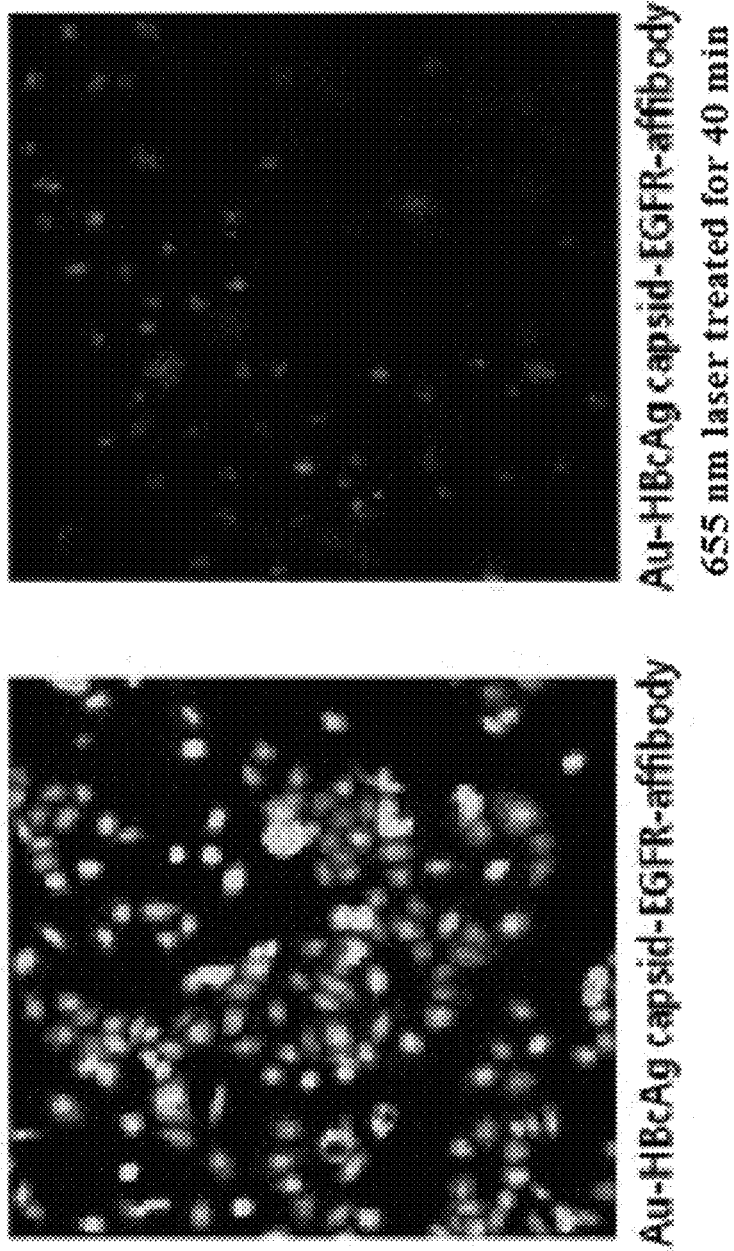
FIG. 5C shows distributions of viable and dead cells immediately after the gold-protein nanoparticle fusion containing a peptide specific for breast cancer cells was introduced into cells and after necrosis was induced by subsequent irradiation of a laser, as analyzed by double staining.

The gold-protein particle fusion of the present invention was analyzed for photothermal therapy performance by measuring the temperature elevation and the consequent necrosis of cancer cells when the cancer cells that engulfed or did not engulf the gold-protein particle fusion of the present invention as described in Example 7 were irradiated with a laser (655 nm, 200 W). In this regard, the cells grown on 35-φ plates were irradiated with laser, and measured for viability using a CCK-8 kit (Dojindo, Japan). Irradiation of a laser into the gold-protein nanoparticle fusion for 40 min generated heat in a higher quantity when a greater concentration of the fusion was used, with the consequent reduced survival of the cancer cells (FIG. 5A). The group treated with the EGFR affibody-conjugated particle fusion was observed to further to be reduced in cell density when irradiated with laser, compared to that treated with EGFR affibody-deficient particle fusion (FIG. 5B). Double staining with calcein AM (live cells stained, green fluorescent) and PI (dead cells stained, red fluorescent) showed that laser irradiation for 40 min in the presence of 25 nM of the gold-protein particle fusion of the present invention induced most of the cancer cells to undergo necrosis, appearing red fluorescent (FIG. 5C).

Figure 6A:
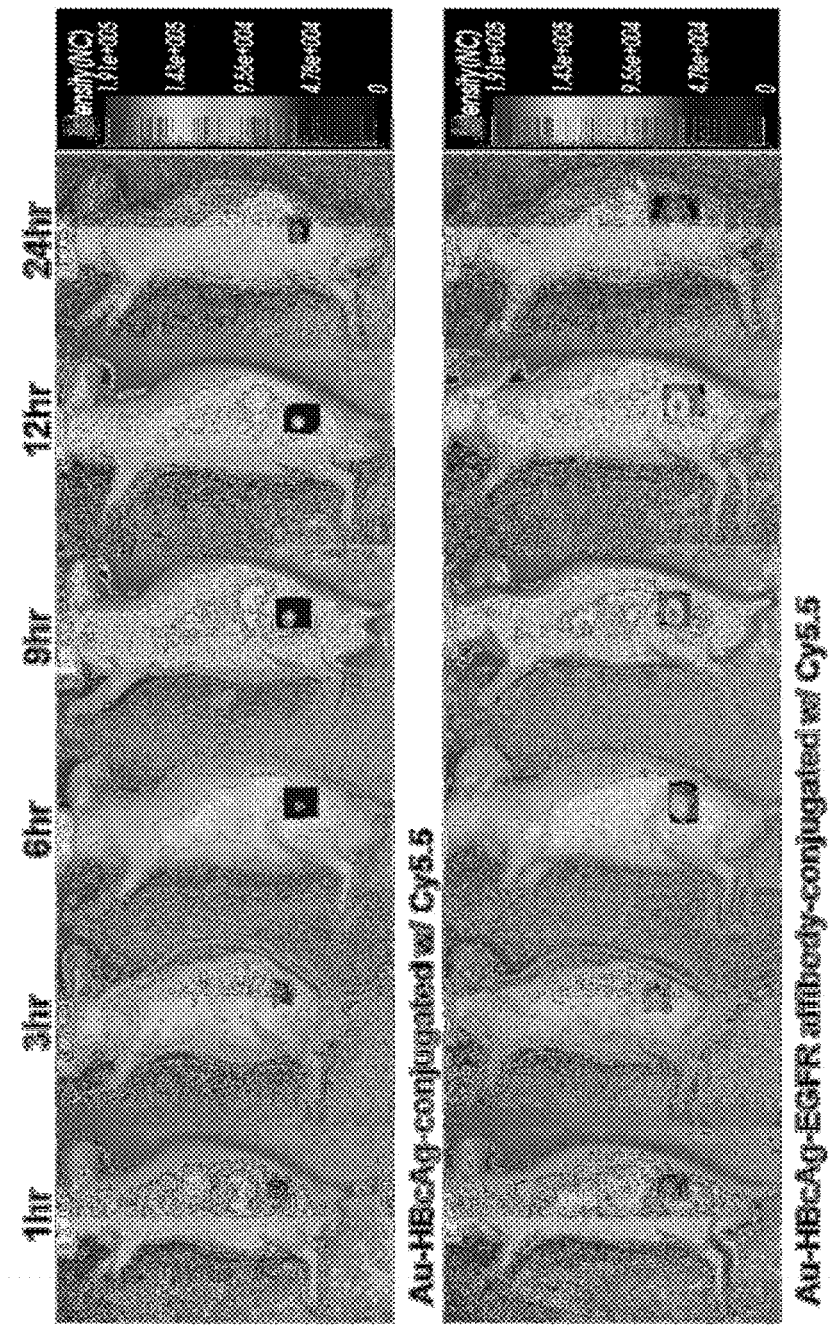
FIG. 6A compares targeting effects of the gold-protein nanoparticle fusions with or without a biodiagnostic peptide (EGFR affibody) specific for breast cancer cells on the object cancer cell line (MDA MB468), showing changes in the distribution of the particles with time after the gold-protein fusions were injected via a tail vein into mice in which the cancer cells had been sufficiently developed.
Figure 6B:
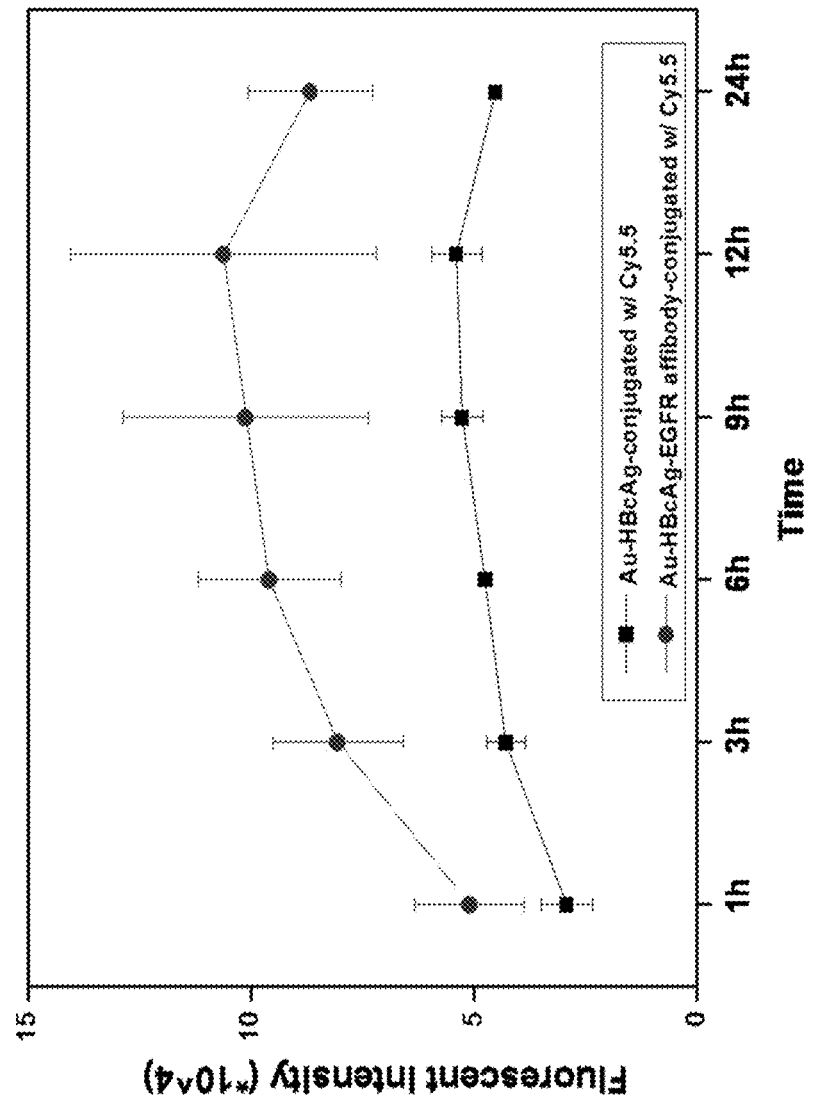
FIG. 6B is a graph in which maximum fluorescent intensities from cancer cells are plotted against time after injection, based on the imaging data of FIG. 6A.

Example 9: In Vivo Assay of HBV Capsid-Derived Chimeric Gold-Protein Nanoparticle Fusion for Specifically Targeting Cancer Cell The HBV capsid-derived chimeric gold-protein nanoparticle fusion of the present invention was in vivo assayed for target directionality toward cancer cells. To mice in which a target cancer cell line (MDA MB468 cell line) had been sufficiently developed, EGFR affibody-containing or deficient gold-protein nanoparticle fusions were injected via the tail vein. The gold-protein nanoparticle fusions was monitored for distribution around the cancer cells from 1 to 24 hrs after injection (FIG. 6A). Maximum fluorescent intensities from cancer cells were tracked for 1 to 24 hrs after injection, and are plotted (FIG. 6B). The group injected with the gold-protein nanoparticle fusion containing the EGFR affibody specific for breast cancer cells exhibited two, on average, to up to three times higher fluorescent intensities, compared to that injected with the EGFR-deficient fusion. These data indicated that the presence of the breast cancer cell-specific peptide (EGFR affibody) allows the fusion to direct toward the target cancer cell line (MDA MB468 cell line) to a higher extent.

Example 10: Assay for Photothermal Therapeutic Effect of HBV Capsid-Derived Chimeric Gold-Protein Nanoparticle Fusion in Response to Laser Irradiation after Intratumoral Injection After intratumoral injection of the HBV capsid-derived chimeric gold-protein nanoparticle fusion into a target cancer cell line MDA MB468 cell line), photothermal therapeutic effects were observed in response to laser irradiation.

Figure 7A:
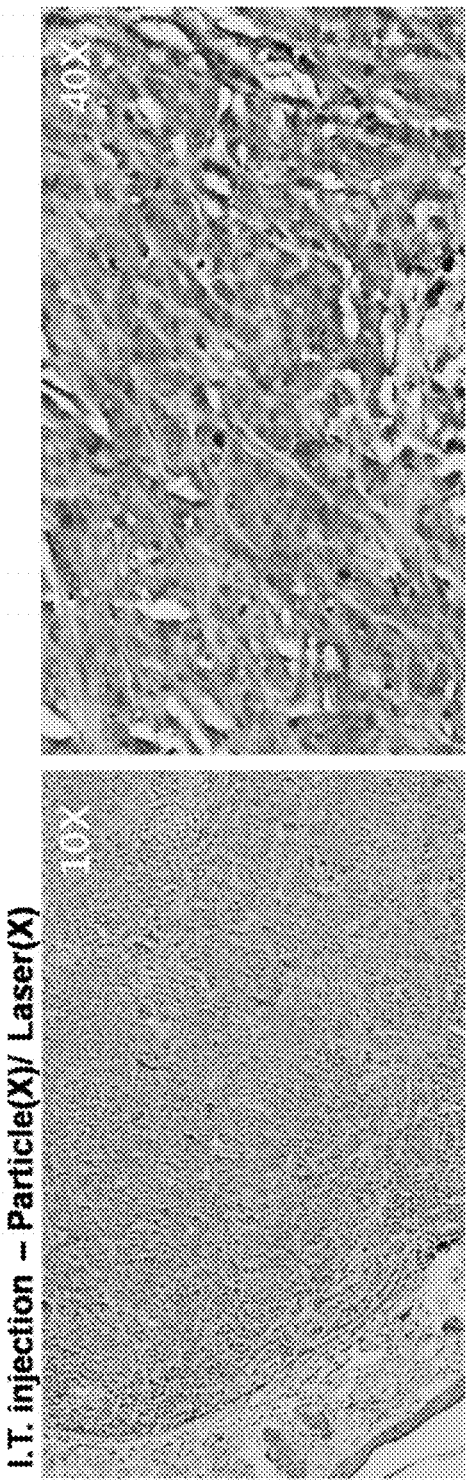
FIGS. 7A through 7E show histological images of cancer cells from mice in which cancer cells had sufficiently been developed after no treatments were performed on the mice, after the gold-protein nanoparticle fusion was injected into the mice, after a laser was irradiated into the mice without injecting the gold-protein nanoparticle fusion, and after the gold-protein nanoparticle fusion was injected into the mice, followed by irradiating a laser for 10 min and for 50 min.
Figure 7B:
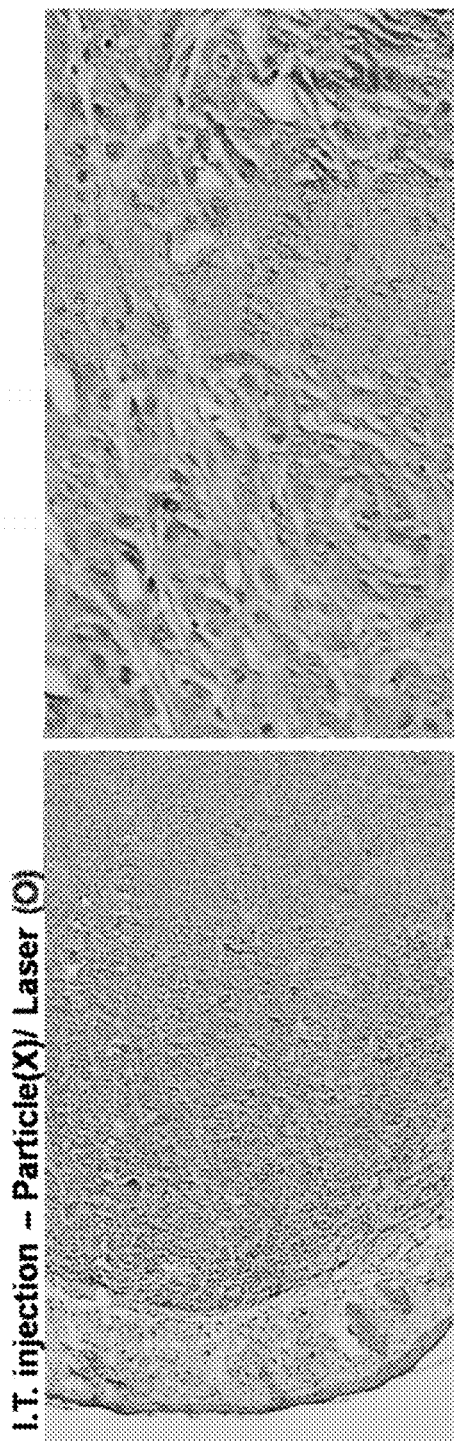
Figure 7C:
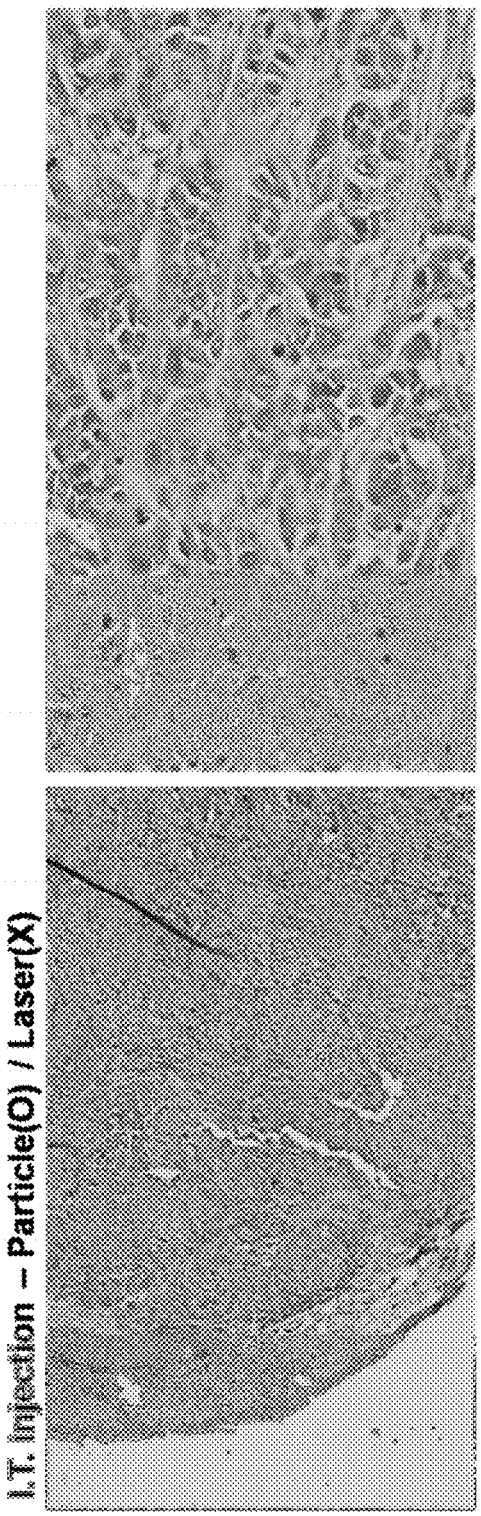
Figure 7D:
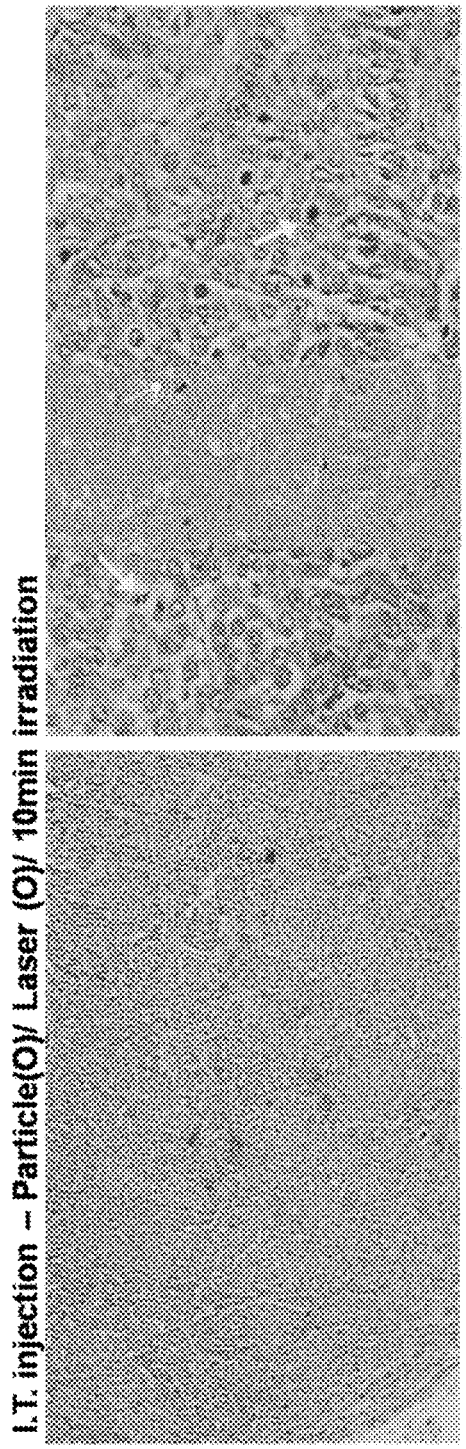
Figure 7E:
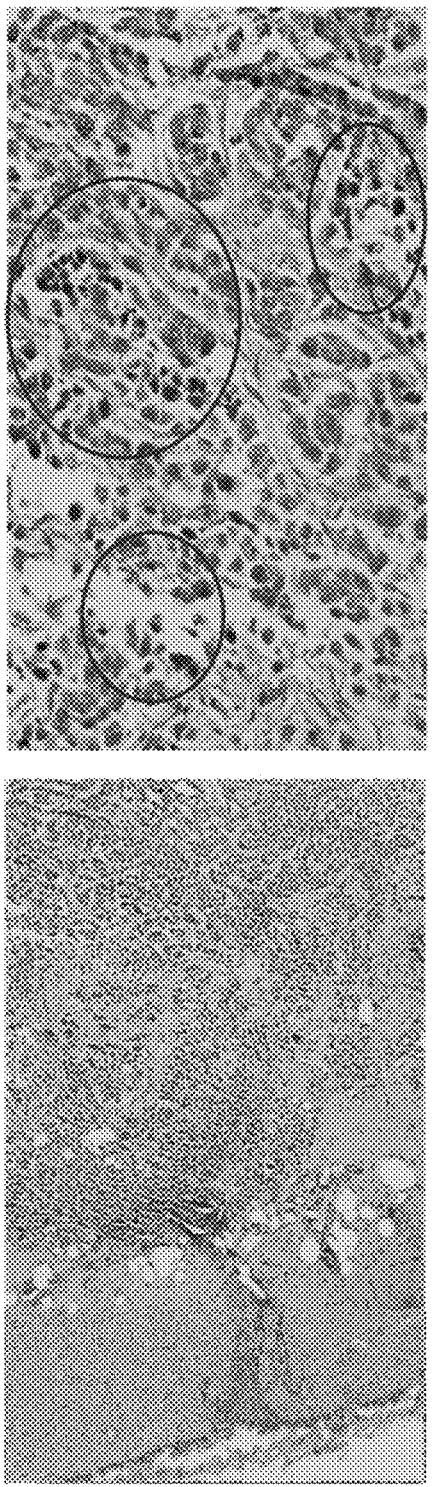

Mice in which the target cancer cells (MDA MB468 cell line) had been sufficiently developed were treated as follows: 1) neither was the gold-protein nanoparticle fusion injected, nor was a laser irradiated (control) (FIG. 7A); 2) the gold-protein nanoparticle fusion was not injected, but a laser was irradiated (FIG. 7B); 3) the gold-protein nanoparticle fusion was injected, but a laser was not irradiated; 4) the gold-protein nanoparticle fusion was injected, and a laser was irradiated for 10 min (FIG. 7D) and 50 min (FIG. 7E). In this experiment, the necrotic effect of the gold-protein nanoparticle in the presence of a laser on cancer cells was examined by histological analysis while the first three experiments were designed to examine effects of the gold-protein nanoparticle or the laser alone on tissue injury.

FIG. 7A shows images of a control to which neither was the gold-protein nanoparticle fusion injected nor was a laser irradiated, so as to present the histological morphology of the cancer cells themselves. FIG. 7B provides images of an experimental group into which a laser was irradiated without injection of the gold-protein nanoparticle fusion, showing whether laser-induced tissue necrosis occurred. In light of the histological image of FIG. 7A, the laser irradiation was observed to not cause necrosis. FIG. 7C shows an image of an experimental group to which the gold-protein nanoparticle fusion was injected, without irradiating a laser, showing whether the gold-protein nanoparticle fusion itself had toxicity. When comparing with the histological image of FIG. 7A, no necrosis occurred in the tissue of this experimental group, indicating that the gold-protein nanoparticle fusion itself was not toxic.

FIGS. 7D and 7E are images of experimental groups to which a laser was irradiated, respectively, for 10 min and 50 min after the injection of the gold-protein nanoparticle fusion, showing the photothermal therapeutic effect of the gold-protein nanoparticle fusion. When a laser was irradiated for 10 min into the experimental group, the tissue started to necrotize as indicated by arrows in FIG. 7D. Sufficient irradiation of a laser for 50 min caused general damage across the tumor as shown in the low-magnification image (left panel) of FIG. 7E. In circle portions of the high-magnification image (right panel) of FIG. 7E, the tumor tissue underwent severe necrosis.

Briefly, it was found that the treatments of 1), 2), or 3) do not bring about significant damage on cancer cells, irradiation of a laser for 10 min induces cancer cells to undergo necrosis, and most cancer cells are necrotized after irradiation of a laser for 50 min, as shown in 4). Through these experiments, photothermal therapy utilizing the gold-protein nanoparticle fusion was sufficiently effective.

Example 11: Effect of Targeting of HBV Capsid-Derived Chimeric Gold-Protein Nanoparticle Fusion on Photothermal Therapy Against Target Cancer Cell Line (MDA MB468) Upon Laser Irradiation after In Vivo Injection After the HBV capsid-derived chimeric gold-protein nanoparticle fusion was injected through the tail vein into mice in which the target cancer cell line (MDA MB468) had been sufficiently developed, the mice were left for a sufficient time before laser irradiation in order for the fusion to target the cancer cell line. Then, an effect of targeting on photothermal therapy was examined.

Mice where the target cancer cell line (MDA MB468) had sufficiently been developed were prepared, and the gold-protein nanoparticle fusion was injected via the tail vein to the mice. It took 9-12 hours for the fusion to target the cancer cell line to the maximum extent as shown in Example 9. Hence, after the mice were left for 9 hrs, their tumor tissues were analyzed (FIG. 8A) or irradiated with a laser for 50 min (FIG. 8B). In addition, 5 days later, tumor sizes were compared between mice that were only irradiated with a laser and those that were injected with the gold-protein nanoparticle fusion and irradiated with a laser (FIGS. 8C and 8D).

Figure 8A:
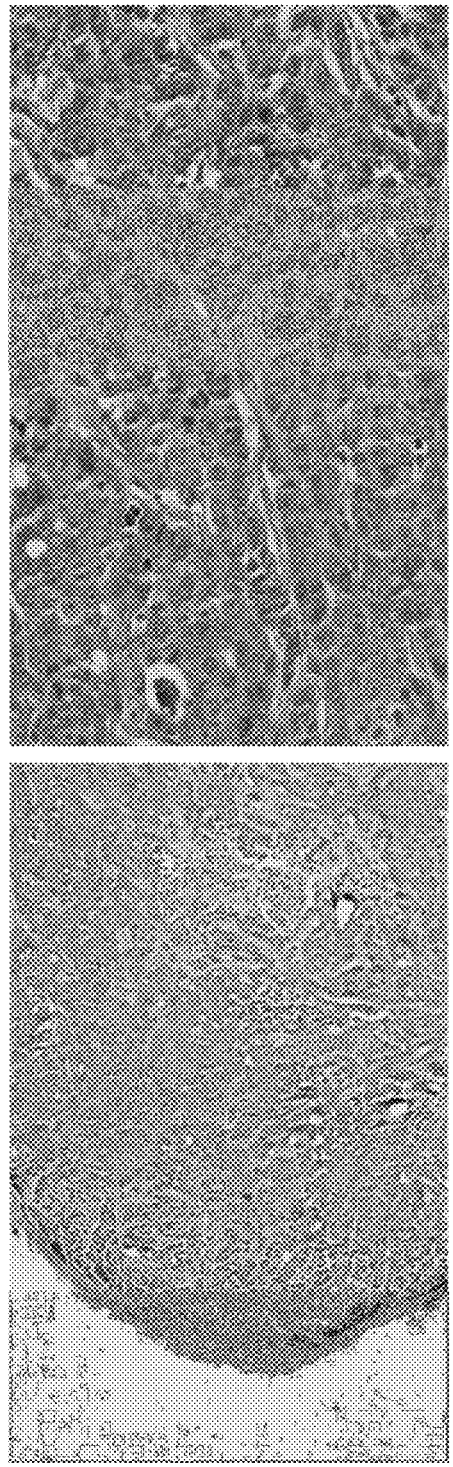
FIGS. 8A through 8D show histological analysis results of cancer cells from cancer-developed mice to which the gold-protein nanoparticle fusion was injected via a tail vein (A) and allowed to target the cancer cells for 9 hrs (A), followed by irradiating a laser for 50 min (B), and cancer cell size results compared between the groups that were only irradiated with a laser and which were injected with the gold-protein nanoparticle fusion and irradiated with a laser, 5 days after the irradiation.
Figure 8B:
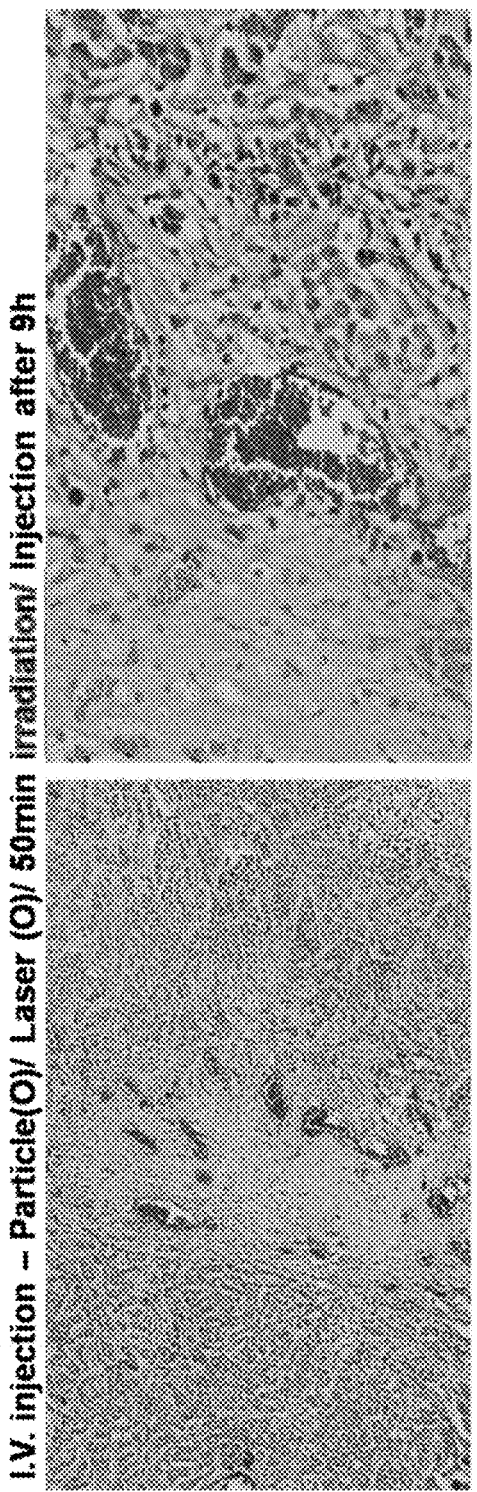
Figure 8C:
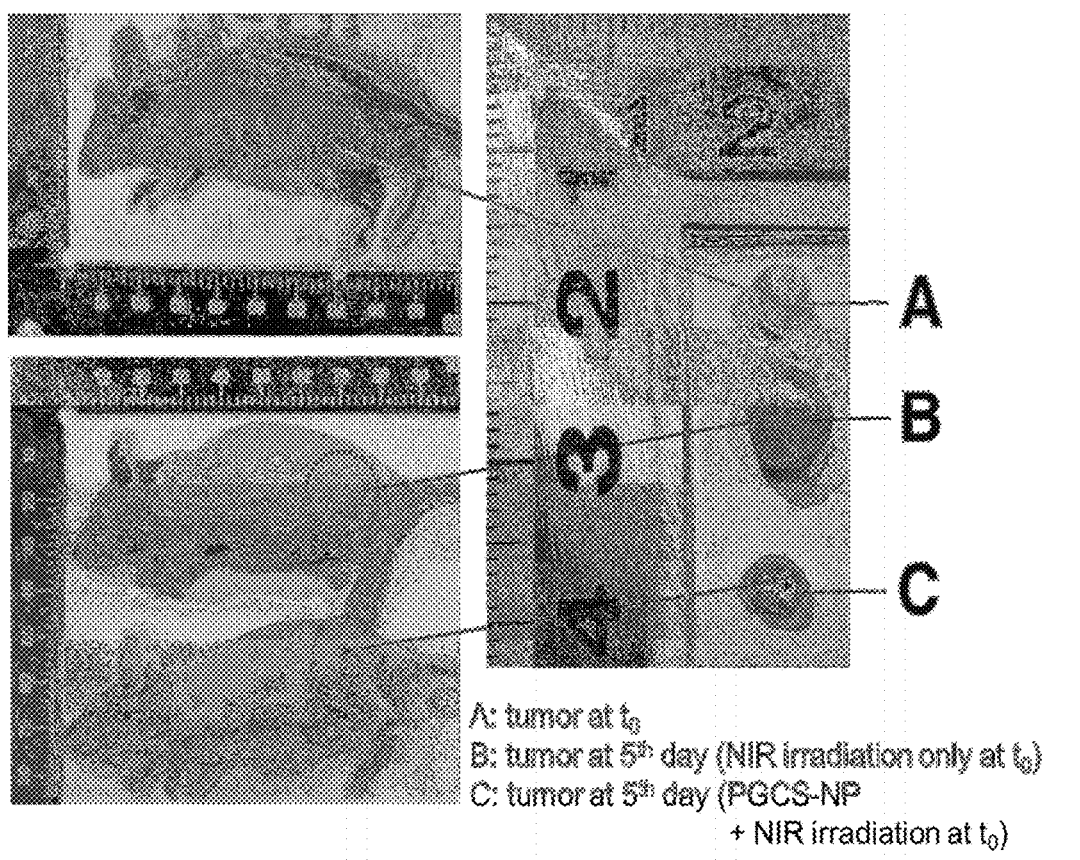
Figure 8D:
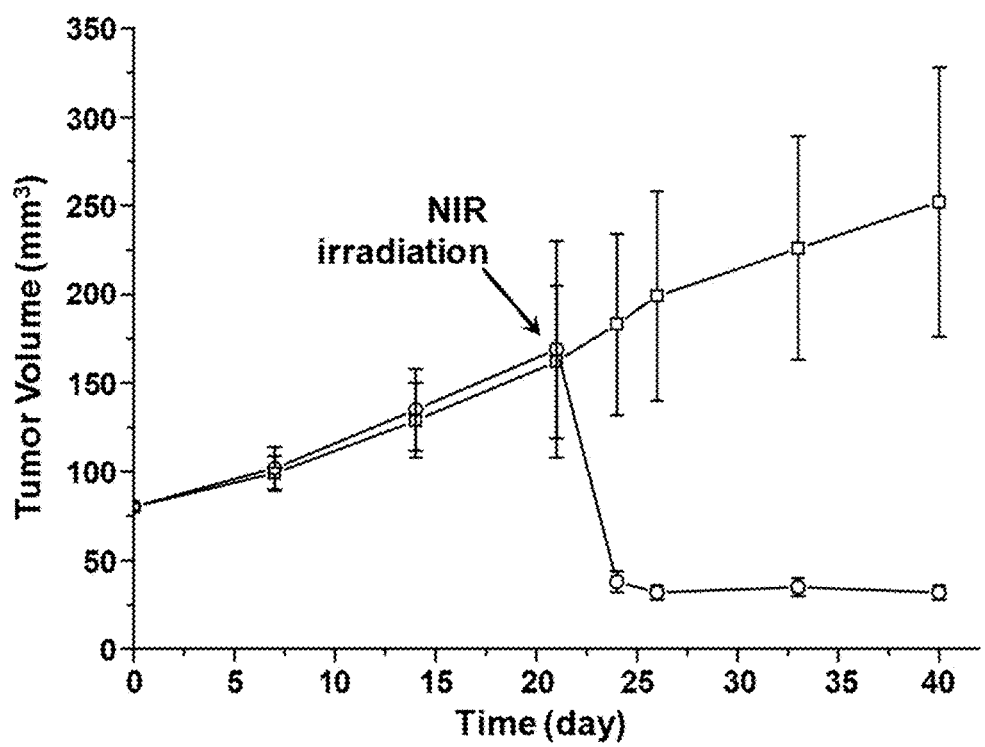
Figure 9:
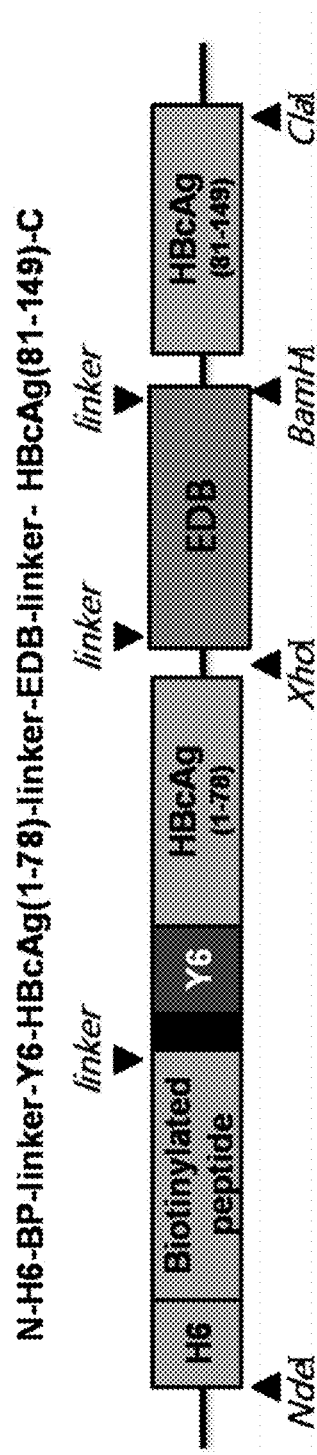
FIG. 9 is a schematic view of an expression vector, containing EDB as a target-oriented peptide, for the preparation of a gold-protein nanoparticle fusion.

FIG. 8A shows histological images of cancer cells from an experimental group into which the gold-protein nanoparticle fusion was injected via the tail vein and then left for 9 hrs so as to target the cancer cells, and is adapted to examine whether the gold-protein nanoparticle fusion itself necrotizes tumors and has toxicity in vivo. As is apparent from the result of the histological analysis, the gold-protein nanoparticle fusion itself did not cause necrosis. Because the gold-protein nanoparticle fusion was demonstrated to target the tumor tissue, the fusion itself has no toxicity.

FIG. 8B shows histological images of cancer cells from an experimental group into which the gold-protein nanoparticle fusion was injected via the tail vein and then left for 9 hrs so as to target the cancer cells before laser irradiation for 50 min to implement photothermal therapy. Comparing the result of FIG. 8A, necrosis occurred across the cancer cells, and intensively in the tumor core, with concomitant vasodilation and hemorrhage in the tumor.

As can be seen, the gold-protein nanoparticle fusion did not induce necrosis in cancer cells by targeting alonein vivo, and thus the gold-protein nanoparticle fusion itself was not toxic to the cancer cells. Only when a laser was irradiated for 50 min after introduction of the gold-protein nanoparticle fusion, the tumor underwent general necrosis, with concomitant vasodilation in the tumor core. In addition, hemorrhage was observed as some cancer cells were necrotized.

FIG. 8C shows images comparing tumor sizes 5 days after the mice were irradiated with a laser without injection of the gold-protein nanoparticle fusion, or were injected with the gold-protein nanoparticle fusion and irradiated for 50 min with a laser. In the experimental group that was only irradiated with a laser, the tumor size increased further. In contrast, the tumor disappeared in the experimental group to which a laser was irradiated after the injection of the gold-protein nanoparticle fusion, leaving a scab on the injury.

FIG. 8D is a graph quantitatively showing the growth tendency of tumors in the two experimental groups and a change in tumor size after laser-induced photothermal therapy.

From the data, it is apparent that the gold-protein nanoparticle fusion of the present invention can be used for photothermal therapy using an NIR laser against cancer after the gold-protein nanoparticle fusion is allowed to target tumor cells. Compared to conventional gold nanoparticles, the gold-protein nanoparticle fusion used in this experiment is a very effective material for photothermal therapy because it has higher structural stability against pH changes in vivo and exhibits higher target directability.

Figure 10:
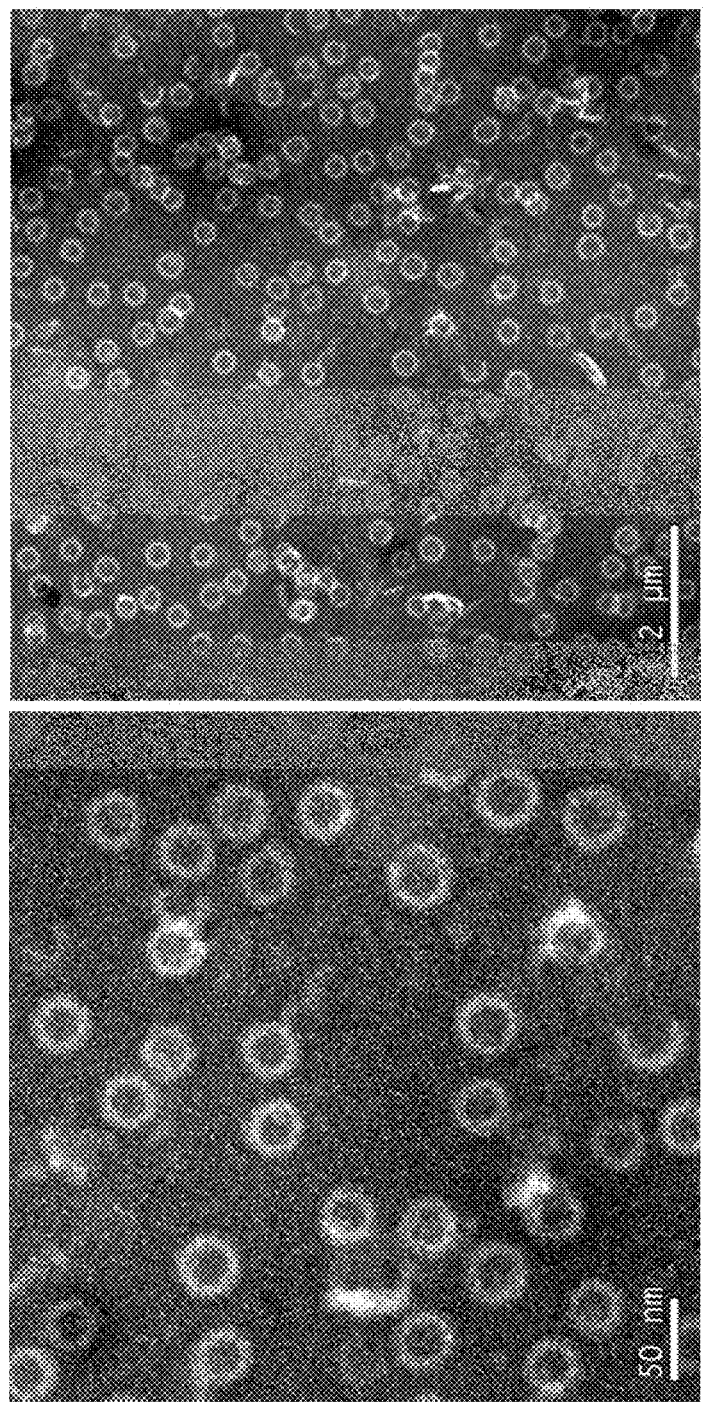
FIG. 10 provides TEM images showing that the recombinant HBV capsid protein containing both EDB and a gold ion reducing peptide forms a stable structure.

Example 12: Construction of Expression Vector for Biosynthesis of HBV Capsid-Derived Chimeric Nanoparticle Instead of the target-oriented peptide for the EGFR, which takes an alpha helical structure, a target-oriented peptide for EDB, which takes a linear structure, was used for the synthesis of an HBV capsid-derived chimeric nanoparticle.

Two gene clones respectively encoding N-NdeI-H6(hexahistidine)-BP(Biotinylated peptides)-Y6(hexatyrosine)-HBVcAg(1-78)-XhoI-C(SEQ ID NO: 2) and N-BamHI-HBVcAg(81-149)-ClaI-C(SEQ ID NO: 3), both derived from an HBV core protein gene (HBVcAg), were acquired by extension PCR using an HBV capsid gene sequence (SEQ ID NO: 1, a 1901-2452 sequence of the NCBI Nucleotide accession number: AF286594) as a template in the presence of primers 1-5, and primer 6 as listed in Table 1, below. In order to substitute P79A80 of HBVcAg with EDB (human fibronectin extradomain B), 5'-XhoI-EDB-BamHI-3' (SEQ ID NO: 16) was obtained by PCR. These gene clones were ligated in serial to plasmid pT7-7 to construct a recombinant plasmid expression vector pT7-7-N-H6-BP-Y6-HBVcAg(1-78)-EDB-HBVcAg(81-149)-C carrying the gene N-H6-BP-Y6-HBVcAg(1-78)-EDB-HBVcAg(81-149)-C(SEQ ID NO: 17) (FIG. 9). After agarose-gel isolation of the recombinant plasmid expression vector, DNA sequencing was carried out to identify the sequence.

Information on primer sequences and templates relevant to the preparation of HBV capsid-derived chimeric nanoparticles will be described in detail, below (Table 2).

1) A first segment was obtained by extension PCR using an HBV capsid protein gene (SEQ ID NO: 1, a 1901-2452 sequence of NCBI Nucleotide accession number: AF286594) as a template in the presence of primers 1 to 5 containing the restriction recognition site NdeI, and primer 6 containing the restriction recognition site XhoI. As a result, a 5'-NdeI-H6-BP-Y6-HBV capsid protein (amino acid sequence 1-78)-XhoI-3' sequence (SEQ ID NO: 2) was obtained as a PCR product.

2) For a second segment, PCR was performed on an HBV capsid protein gene as a template in the presence of primers 7 and 8 containing the restriction recognition sites BamHI and ClaI, respectively. As a result, a 5'-BamHI-HBV capsid protein (amino acid sequence 81-149)-ClaI-3' sequence (SEQ ID NO: 3) was obtained as a PCR product.

3) A third segment was obtained by performing PCR on an EDB nucleotide sequence as a template in the presence of primers 11 and 12 containing the restriction recognition sites XhoI and BamHII, respectively. As a result, a 5'-XhoI-EDB-BamHI-3' sequence (SEQ ID NO: 16) was acquired as a PCR product.

The PCR products obtained above were sequentially inserted into a pT7-7 vector to construct a recombinant expression vector pT7-7-N-H6-BP-Y6-HBVcAg(1-78)-EDB-HBVcAg(81-149)-C, which can express an HBV capsid-derived functional moiety (hexatyrosine) capable of inducing the reduction of gold ions, and an EDB binding specifically to human glioblastoma and astrocytoma cell line (U87MG) (FIG. 9).

3) Comparison was made of the affinity of EDB for cancer cells. For this, extension PCR was performed using primers 1 to 5, and primer 8 containing ClaI. The PCR product thus obtained was inserted into a pT7-7 vector to construct a recombinant expression vector carrying a gene that encodes an HBV capsid-derived functional moiety (hexatyrosine) capable of inducing the reduction of gold ions. The recombinant expression vector was used as a control for EDB (FIG. 1B).

TABLE 2

| | | |
|---|---|---|
| Primer 11 (SEQ ID NO: 18) | 5' XhoI-EDB | CTCGAG CAT AGC TGC AGC TCC CCG ATT CAG |
| Primer 12 (SEQ ID NO: 19) | 3' BamHI-EDB | GGA TCC CGG CTG CTG TTC CAG ACG AAT AAT GCC |

After the transformation of the vector pT7-7-N-H6-BP-Y6-HBVcAg(1-78)-EDB-HBVcAg(81-149)-C, the chimeric protein was biosynthesized and purified in the same manners as in Examples 2 and 3. The chimeric protein was subjected to structural analysis through TEM as described in Example 5 (FIG. 10). As can be seen in FIG. 10, a HBV capsid protein containing a target-oriented peptide and a gold ion reducing peptide was stably formed, like the HBV capsid protein using the target-oriented peptide for targeting EGFR of Example 1.

TEST EXAMPLES

Figure 11A:
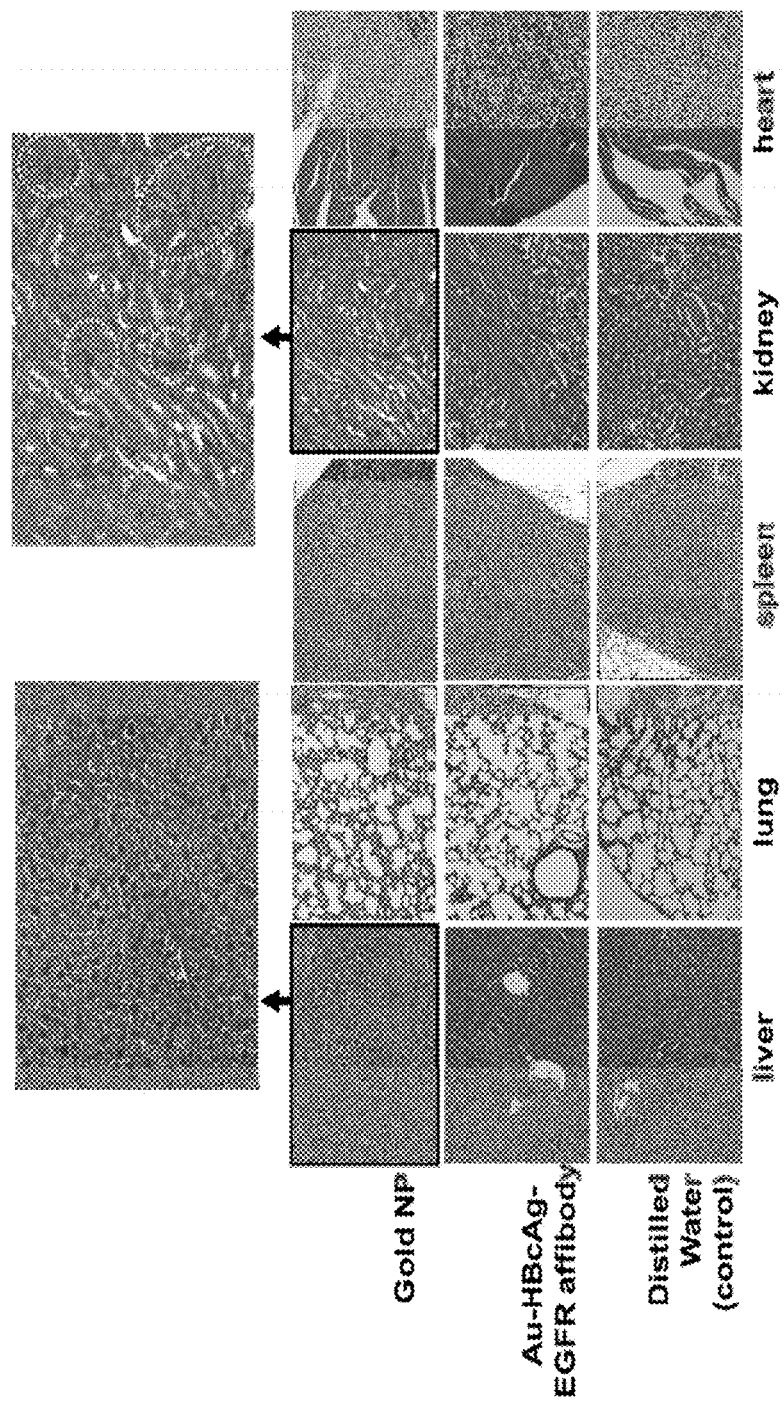
FIGS. 11A and 11B show in vivo toxicities compared between a 40-nm gold nanoparticle and the gold-protein nanoparticle fusion of the present invention, with deionized water serving as a control.
Figure 11B:
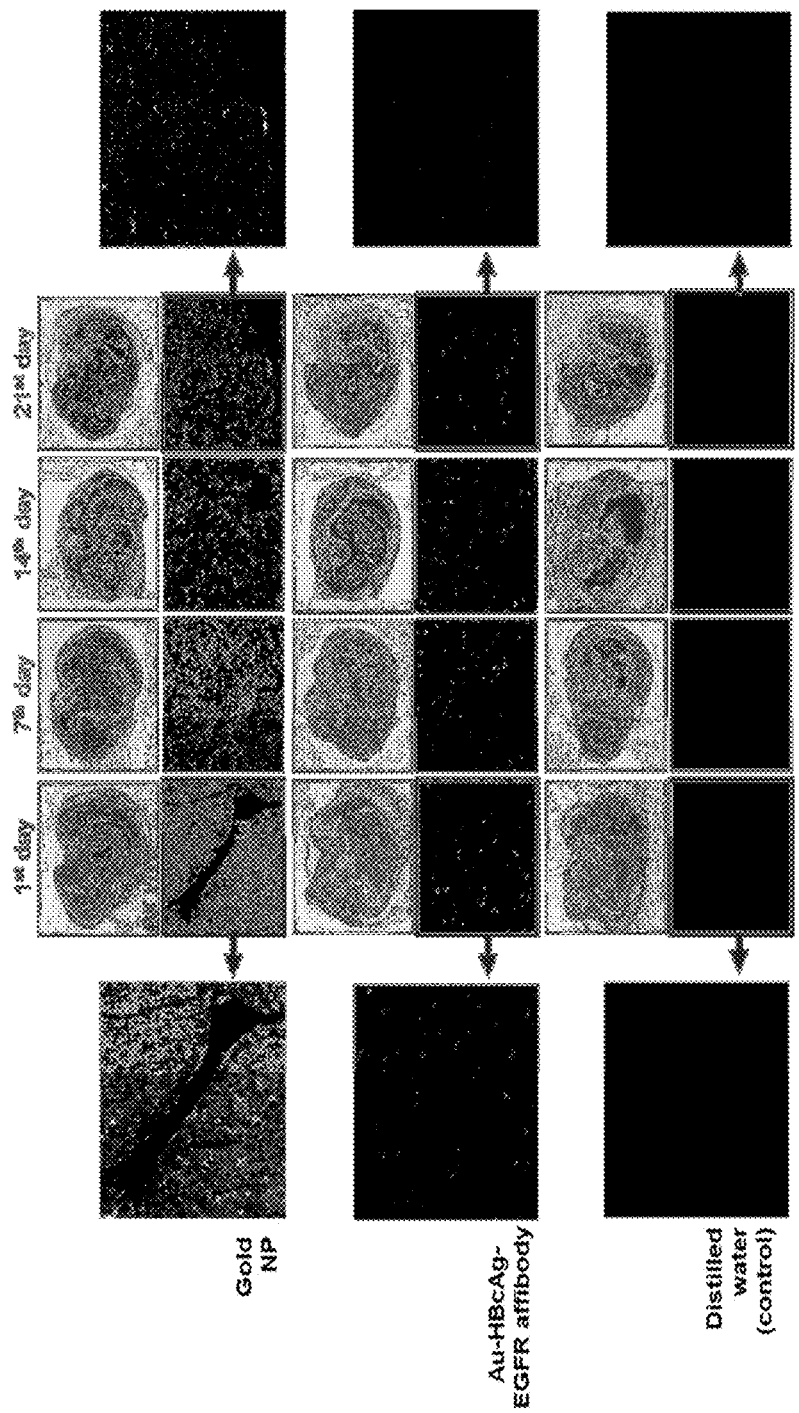

Test Example 1: Comparison of In Vivo Toxicity Between Gold-Protein Nanoparticle Fusion and 40-Nm Gold Nanoparticle With regard to in vivo toxicity, the gold-protein nanoparticle fusion of the present invention was compared with a 40-nm gold nanoparticle, both similar in size, while deionized water was used as a control. One day after the injection of the samples into the body, five main organs including the liver, the lungs, the kidneys, the pancreas, and the heart was biopsied to examine the in vivo toxicity of the samples (FIG. 11A). In the group injected with the gold nanoparticle, partial hemorrhage, edema, and macrophages for digesting a toxic substance were detected, indicating that the gold nanoparticle was significantly toxic. In contrast, no noticeable changes were observed in the group injected with the same concentration of the gold-protein nanoparticle fusion, as in the group administered with the control deionized water. In order to investigate the accumulation of the two substances in vivo, the livers were anatomically analyzed and visualized at regular intervals of 7 days for 21 days by dark-field microscopy in which gold objects present in tissues scatter light and appear bright (FIG. 11B).

As can be seen, the gold nanoparticles were not discharged from the liver, but were accumulated at a high concentration for 21 days, appearing deep dark in the dark-field image whereas the livers from the mice injected with the gold-protein nanoparticle fusion exhibited normal tissue states without the detection of color changes in the anatomical images. Further, the gold-protein nanoparticle fusion was discharged from the body within a week, so that almost all gold particles disappeared 7 days after injection in the dark-field images.

As is apparent from the data obtained above, the gold-protein nanoparticle fusion of the present invention is free of the in vivo toxicity of conventional gold nanoparticles, and thus can be applied as a biocompatible material for use in vivo.

Test Exaple 2: Use as CT Contrast Agent after In Vivo Application (Intratumoral Injection)

Figure 12:
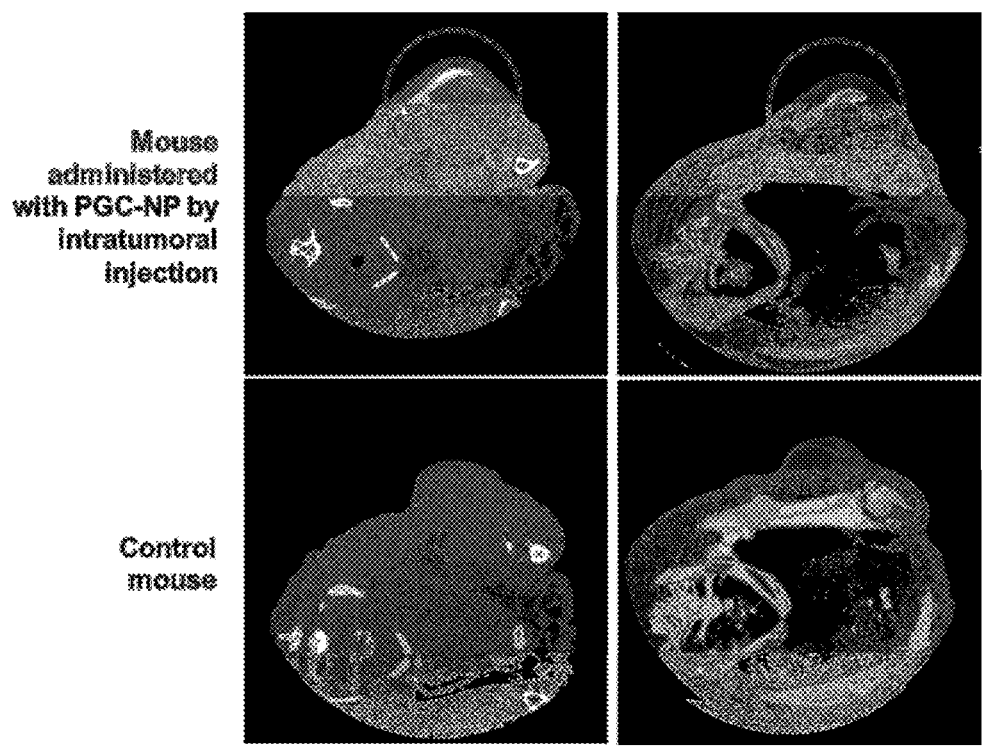
FIG. 12 shows X-ray CT images of mice after intratumoral injection of the gold-protein nanoparticle fusion.

Examination was made of the usefulness of the gold-protein nanoparticle fusion as an X-ray CT contrast agent by comparing two groups that were administered with the gold-protein nanoparticle fusion by intratumoral injection and were not administered, respectively (FIG. 12). Because it provides a high contrast against the background when irradiated with an X-ray, gold can be used as a contrast agent. Accordingly, the gold-protein nanoparticle fusion of the present invention, if proven as having a contrasting effect, can be used as a very effective contrast agent thanks to the in vivo target directability shown in Example 9. After intratumoral injection of the gold-protein nanoparticle, the tumor was visualized at a brightness level similar to that of neighbor bones, as analyzed by X-ray computed tomography (CT).

Hence, the gold-protein nanoparticle fusion of the present invention is proven as a CT contrast agent.

The invention claimed is:

1. A recombinant self-assembled protein, comprising a target-oriented peptide fused to an HBV capsid protein as a self-assembled protein and a gold ion reducing peptide self-assembled.

2. The recombinant self-assembled protein of claim 1, wherein the target-oriented peptide is introduced into a spike region of the recombinant HBV capsid protein.

3. The recombinant self-assembled protein of claim 1, wherein the target-oriented peptide targets EGFR (epidermal growth factor receptor) or EDB (human fibronectin extra domain B).

4. The recombinant self-assembled protein of claim 1, wherein the target-oriented peptide is located between two sequences of amino acids 1-78 and 81-149 on the recombinant HBV capsid protein.

5. The recombinant self-assembled protein of claim 1, wherein the target-oriented peptide is inserted in two or more copies into the recombinant HBV capsid protein.

6. The recombinant self-assembled protein of claim 1, wherein the gold ion reducing peptide comprising at least one selected from the group consisting of two or more tyrosine residues, two or more histidine residues, and two or more cysteine residues.

7. The recombinant self-assembled protein of claim 1, wherein the gold ion reducing peptide is introduced into an N- or C-terminus of the recombinant self-assembled protein.

8. The recombinant self-assembled protein of claim 1, further comprising a gold nanoparticle size-controlling peptide in a vicinity of the gold ion reducing peptide.

9. The recombinant self-assembled protein of claim 8, wherein the gold nanoparticle size-controlling peptide is a biotinylated peptide.

10. The recombinant self-assembled protein of claim 8, further comprising a linker peptide between the gold ion reducing peptide and the gold nanoparticle size-controlling peptide.

11. A recombinant self-assembled protein nanoparticle, comprising copies of the recombinant self-assembled protein of claim 1.

12. A method for preparing a gold-protein particle fusion, comprising reacting the recombinant self-assembled protein nanoparticle of claim 11 with a gold precursor to form a gold nanoparticle on the recombinant self-assembled protein nanoparticle.

13. The method of claim 12, wherein the gold precursor is chloro(trimethylphosphine)gold ($AuClP(CH_3)_3$), potassium tetrachloroaurate (III) ($KAuCl_4$), sodium chloroaurate ($NaAuCl_4$), chloroauric acid ($HAuCl_4$), sodium bromoaurate ($NaAuBr_4$), gold chloride ($AuCl$), gold chloride (III) ($AuCl_3$), or gold bromide ($AuBr_3$).

14. A gold-protein particle fusion in which a gold nanoparticle is formed on the recombinant capsid nanoparticle of claim 11.

15. The gold-protein particle fusion of claim 14 which is used in preparing a medicine for photothermal therapy.

16. The gold-protein particle fusion of claim 15, wherein the photothermal therapy is to treat cancer.

17. A method for preparing the recombinant self-assembled protein of claim 1, comprising:

a) cloning a gene coding for a self-assembled protein;

b) cloning a gene including a nucleotide sequence coding for a target-oriented peptide fused to an HBV capsid protein for insertion into the self-assembled protein;

c) constructing an expression vector containing the clones by ligation; and d) transforming the expression vector into a host to express the recombinant self-assembled protein.

* * * * *

SEQUENCE LISTING

```
<160> NUMBER OF SEQ ID NOS: 22

<210> SEQ ID NO 1
<211> LENGTH: 450
<212> TYPE: DNA
<213> ORGANISM: Hepatitis B virus

<400> SEQUENCE: 1
atggacattg acccgtataa agaatttgga gcttctgtgg agttactctc ttttttgcct      60
tctgacttct ttccttctat tcgagatctc ctcgacaccg cctctgctct gtatcgggag     120
gccttagagt ctccggaaca ttgttcacct caccatacag cactcaggca agctattctg     180
tgttggggtg agttgatgaa tctggccacc tgggtgggaa gtaatttgga agacccagca     240
tccagggaat tagtagtcag ctatgtcaac gttaatatgg gcctaaaaat cagacaacta     300
ttgtggtttc acatttcctg tcttactttt ggaagagaaa ctgttcttga gtatttggtg     360
tcttttggag tgtggattcg cactcctccc gcttacagac caccaaatgc ccctatctta     420
tcaacacttc cggaaactac tgttgtttaa                                      450

<210> SEQ ID NO 2
<211> LENGTH: 423
<212> TYPE: DNA
<213> ORGANISM: Artificial Sequence
<220> FEATURE:
<223> OTHER INFORMATION: N-NdeI-H6-BP-Y6-HBVcAg(1-78)-XhoI-C
```

```
<400> SEQUENCE: 2
catatgcatc accatcacca tcacatggcg tctagtctgc gtcagattct ggattctcag      60
aaaatggaat ggcgttctaa tgcgggtggc tctggtggcg aagtgggggg aggcactgga     120
ggtggcagcg gcggtgggta ctattactat tactatgaca ttgacccgta taaagaattt     180
ggagcttctg tggagttact ctcttttttg ccttctgact tctttccttc tattcgagat     240
ctcctcgaca ccgcctctgc tctgtatcgg gaggccttag agtctccgga acattgttca     300
cctcaccata cagcactcag gcaagctatt ctgtgttggg gtgagttgat gaatctggcc     360
acctgggtgg aagtaatttt ggaagacggt ggcggaggga gtgggggggg cggtactctc     420
gag                                                                  423

<210> SEQ ID NO 3
<211> LENGTH: 249
<212> TYPE: DNA
<213> ORGANISM: Artificial Sequence
<220> FEATURE:
<223> OTHER INFORMATION: N-BamHI-HBVcAg(81-149)-ClaI -C

<400> SEQUENCE: 3
ggatccggtg gcggagggtc tgggggaggc ggttccaggg aattagtagt cagctatgtc      60
aacgttaata tgggcctaaa atcagacaac tattgtggt ttcacatttc ctgtcttact      120
tttggaagag aaactgttct tgagtatttg gtgtcttttg gagtgtggat acgcactcct     180
cccgcttaca gaccaccaaa tgcccctatc ttatcaacac ttccggaaac tactgttgtt     240
taaatcgat                                                            249

<210> SEQ ID NO 4
<211> LENGTH: 366
<212> TYPE: DNA
<213> ORGANISM: Artificial Sequence
<220> FEATURE:
<223> OTHER INFORMATION: 5'-XhoI-EGFR affibody-BamHI-3'

<400> SEQUENCE: 4
ctcgaggtgg ataacaaatt taacaaagaa atgtgggcgg cgtgggaaga aattcgtaac      60
ctgccgaacc tgaacggctg gcagatgacc gcgtttattg cgagcctggt ggatgatccg     120
agccagagcg cgaacctgct ggcggaagcg aaaaaactga acgatgcgca ggcgccgaaa     180
gaattcgtgg ataacaaatt taacaaagaa atgtgggcgg cgtgggaaga aattcgtaac     240
ctgccgaacc tgaacggctg gcagatgacc gcgtttattg cgagcctggt ggatgatccg     300
agccagagcg cgaacctgct ggcggaagcg aaaaaactga acgatgcgca ggcgccgaaa     360
ggatcc                                                               366

<210> SEQ ID NO 5
<211> LENGTH: 1026
<212> TYPE: DNA
<213> ORGANISM: Artificial Sequence
<220> FEATURE:
<223> OTHER INFORMATION: N-H6-BP-Y6-HBVcAg(1-78)- EGFR affibody-
      HBVcAg(81-149)-C

<400> SEQUENCE: 5
catatgcatc accatcacca tcacatggcg tctagtctgc gtcagattct ggattctcag      60
aaaatggaat ggcgttctaa tgcgggtggc tctggtggcg aagtgggggg aggcactgga     120
ggtggcagcg gcggtgggta ctattactat tactatgaca ttgacccgta taaagaattt     180
```

```
ggagcttctg tggagttact ctctttttg ccttctgact tctttccttc tattcgagat    240
ctcctcgaca ccgcctctgc tctgtatcgg gaggccttag agtctccgga acattgttca    300
cctcaccata cagcactcag gcaagctatt ctgtgttggg gtgagttgat gaatctggcc    360
acctgggtgg gaagtaattt ggaagacggt ggcggaggga gtggggggg cggtactctc     420 gaggtggata acaaatttaa caaagaaatg tgggcggcgt gggaagaaat tcgtaacctg    480
ccgaacctga acggctggca gatgaccgcg tttattgcga gcctggtgga tgatccgagc    540
cagagcgcga acctgctggc ggaagcgaaa aaactgaacg atgcgcaggc gccgaaagaa    600
ttcgtggata acaaatttaa caaagaaatg tgggcggcgt gggaagaaat tcgtaacctg    660
ccgaacctga acggctggca gatgaccgcg tttattgcga gcctggtgga tgatccgagc    720
cagagcgcga acctgctggc ggaagcgaaa aaactgaacg atgcgcaggc gccgaaagga    780
tccggtggcg gagggtctgg gggaggcggt tccagggaat tagtagtcag ctatgtcaac    840
gttaatatgg gcctaaaaat cagacaacta ttgtggtttc acatttcctg tcttactttt    900
ggaagagaaa ctgttcttga gtatttggtg tcttttggag tgtggatacg cactcctccc    960
gcttacagac caccaaatgc ccctatctta tcaacacttc cggaaactac tgttgtttaa    1020
atcgat                                                               1026

<210> SEQ ID NO 6
<211> LENGTH: 42
<212> TYPE: DNA
<213> ORGANISM: Artificial Sequence
<220> FEATURE:
<223> OTHER INFORMATION: Primer 1

<400> SEQUENCE: 6
catatgcatc accatcacca tcacatggcg tctagtctgc gt                        42

<210> SEQ ID NO 7
<211> LENGTH: 50
<212> TYPE: DNA
<213> ORGANISM: Artificial Sequence
<220> FEATURE:
<223> OTHER INFORMATION: Primer 2

<400> SEQUENCE: 7
atggcgtcta gtctgcgtca gattctggat tctcagaaaa tggaatggcg                50

<210> SEQ ID NO 8
<211> LENGTH: 51
<212> TYPE: DNA
<213> ORGANISM: Artificial Sequence
<220> FEATURE:
<223> OTHER INFORMATION: Primer 3

<400> SEQUENCE: 8
cagaaaatgg aatggcgttc taatgcgggt ggctctggtg gcggaagtgg g              51

<210> SEQ ID NO 9
<211> LENGTH: 51
<212> TYPE: DNA
<213> ORGANISM: Artificial Sequence
<220> FEATURE:
<223> OTHER INFORMATION: Primer 4

<400> SEQUENCE: 9
ggtggcggaa gtgggggagg cactggaggt ggcggcggtg ggtactatta c              51
```

```
<210> SEQ ID NO 10
<211> LENGTH: 48
<212> TYPE: DNA
<213> ORGANISM: Artificial Sequence
<220> FEATURE:
<223> OTHER INFORMATION: Primer 5

<400> SEQUENCE: 10
ggcggtgggt actattacta ttactatgac attgacccgt ataaagaa                        48

<210> SEQ ID NO 11
<211> LENGTH: 26
<212> TYPE: DNA
<213> ORGANISM: Artificial Sequence
<220> FEATURE:
<223> OTHER INFORMATION: Primer 6

<400> SEQUENCE: 11
ctcgaggtct tccaaattac ttccca                                                26

<210> SEQ ID NO 12
<211> LENGTH: 27
<212> TYPE: DNA
<213> ORGANISM: Artificial Sequence
<220> FEATURE:
<223> OTHER INFORMATION: Primer 7

<400> SEQUENCE: 12
ggatcctcca gggaattagt agtcagc                                               27

<210> SEQ ID NO 13
<211> LENGTH: 33
<212> TYPE: DNA
<213> ORGANISM: Artificial Sequence
<220> FEATURE:
<223> OTHER INFORMATION: Primer 8

<400> SEQUENCE: 13
atcgatttaa acaacagtag tttccggaag tgt                                        33

<210> SEQ ID NO 14
<211> LENGTH: 27
<212> TYPE: DNA
<213> ORGANISM: Artificial Sequence
<220> FEATURE:
<223> OTHER INFORMATION: Primer 9

<400> SEQUENCE: 14
ctcgaggtgg ataacaaatt taacaaa                                               27

<210> SEQ ID NO 15
<211> LENGTH: 42
<212> TYPE: DNA
<213> ORGANISM: Artificial Sequence
<220> FEATURE:
<223> OTHER INFORMATION: Primer 10

<400> SEQUENCE: 15
ggatcctttc ggcgcctgcg catcgttcag ttttttcgct tc                              42

<210> SEQ ID NO 16
<211> LENGTH: 204
<212> TYPE: DNA
<213> ORGANISM: Artificial Sequence
<220> FEATURE:
<223> OTHER INFORMATION: 5'-XhoI-EDB-BamHI-3'
```

<400> SEQUENCE: 16

```
ctcgagcata gctgcagctc cccgattcag ggcagctgga cctgggaaaa cggcaaatgg      60
acctggaaag gcattattcg tctggaacag cagccggaat tcctcgagca tagctgcagc     120
tccccgattc agggcagctg gacctgggaa acggcaaat ggacctggaa aggcattatt     180
cgtctggaac agcagccggg atcc                                            204
```

<210> SEQ ID NO 17
<211> LENGTH: 864
<212> TYPE: DNA
<213> ORGANISM: Artificial Sequence
<220> FEATURE:
<223> OTHER INFORMATION: N-H6-BP-Y6-HBVcAg(1-78)-EDB-HBVcAg(81-149)-C

<400> SEQUENCE: 17

```
catatgcatc accatcacca tcacatggcg tctagtctgc gtcagattct ggattctcag      60
aaaatggaat ggcgttctaa tgcgggtggc tctggtggcg aagtggggg aggcactgga     120
ggtggcagcg gcggtgggta ctattactat tactatgaca ttgacccgta taagaattt     180
ggagcttctg tggagttact ctcttttttg ccttctgact tctttccttc tattcgagat     240
ctcctcgaca ccgcctctgc tctgtatcgg gaggccttag agtctccgga acattgttca     300
cctcaccata cagcactcag gcaagctatt ctgtgttggg gtgagttgat gaatctggcc     360
acctgggtgg aagtaatttt ggaagacggt ggcggaggga gtgggggggg cggtactctc     420
gagcatagct gcagctcccc gattcagggc agctggacct gggaaaacgg caaatggacc     480
tggaaaggca ttattcgtct ggaacagcag ccggaattcc tcgagcatag ctgcagctcc     540
ccgattcagg gcagctggac ctgggaaaac ggcaaatgga cctggaaagg cattattcgt     600
ctggaacagc agccgggatc cggtggcgga gggtctgggg gaggcggttc agggaatta     660
gtagtcagct atgtcaacgt taatatgggc taaaaaatca gacaactatt gtggtttcac     720
atttcctgtc ttacttttgg aagagaaact gttcttgagt atttggtgtc ttttggagtg     780
tggatacgca ctcctcccgc ttacagacca ccaaatgccc ctatcttatc aacacttccg     840
gaaactactg ttgtttaaat cgat                                            864
```

<210> SEQ ID NO 18
<211> LENGTH: 30
<212> TYPE: DNA
<213> ORGANISM: Artificial Sequence
<220> FEATURE:
<223> OTHER INFORMATION: Primer 11

<400> SEQUENCE: 18

```
ctcgagcata gctgcagctc cccgattcag                                       30
```

<210> SEQ ID NO 19
<211> LENGTH: 33
<212> TYPE: DNA
<213> ORGANISM: Artificial Sequence
<220> FEATURE:
<223> OTHER INFORMATION: Primer 12

<400> SEQUENCE: 19

```
ggatcccggc tgctgttcca gacgaataat gcc                                   33
```

<210> SEQ ID NO 20
<211> LENGTH: 6
<212> TYPE: PRT

-continued

```
<213> ORGANISM: Artificial Sequence
<220> FEATURE:
<223> OTHER INFORMATION: Gold ion reducing peptide

<400> SEQUENCE: 20

Tyr Tyr Tyr Tyr Tyr Tyr
1               5

<210> SEQ ID NO 21
<211> LENGTH: 13
<212> TYPE: PRT
<213> ORGANISM: Artificial Sequence
<220> FEATURE:
<223> OTHER INFORMATION: Gold ion reducing peptide

<400> SEQUENCE: 21

Tyr Ala His His Tyr Ala His His Tyr Ala Ala Asp Tyr
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Flag

<400> SEQUENCE: 22

Asp Tyr Lys Asp Asp Asp Asp Lys
1               5
```